United States Patent [19]
LaVallie et al.

[11] Patent Number: 5,986,056
[45] Date of Patent: Nov. 16, 1999

[54] CHORDIN COMPOSITIONS

[76] Inventors: Edward R. LaVallie, 90 Green Meadow Dr., Tewksbury, Mass. 01876; Lisa A. Racie, 124 School St., Acton, Mass. 01720; Edward M. DeRobertis, 16958 Dulce Ynez La., Pacific Palisades, Calif. 90272

[21] Appl. No.: 09/130,032

[22] Filed: Aug. 4, 1998

Related U.S. Application Data

[60] Division of application No. 08/749,169, Nov. 14, 1996, Pat. No. 5,846,770, which is a continuation-in-part of application No. 08/343,760, Nov. 22, 1994, Pat. No. 5,679,783.

[51] Int. Cl.$^6$ .............................. C07K 14/46; C12P 21/00
[52] U.S. Cl. .......................................... 530/350; 435/69.1
[58] Field of Search ............................ 530/350; 435/69.1

[56] References Cited

U.S. PATENT DOCUMENTS

| | | | |
|---|---|---|---|
| 5,013,649 | 5/1991 | Wang et al. | 435/69.1 |
| 5,071,834 | 12/1991 | Burton et al. | 514/12 |
| 5,106,748 | 4/1992 | Wozney et al. | 435/252.3 |
| 5,108,922 | 4/1992 | Wang et al. | 435/240.2 |
| 5,116,738 | 5/1992 | Wang et al. | 435/69.1 |
| 5,141,905 | 8/1992 | Rosen et al. | 435/69.1 |
| 5,166,322 | 11/1992 | Shaw et al. | 530/351 |
| 5,168,050 | 12/1992 | Hammonds, Jr. et al. | 435/69.1 |
| 5,187,076 | 2/1993 | Wozney et al. | 435/69.1 |
| 5,679,783 | 10/1997 | DeRobertis et al. | 536/23.5 |

FOREIGN PATENT DOCUMENTS

| | | |
|---|---|---|
| WO 91/18098 | 11/1991 | WIPO . |
| WO 93/00432 | 1/1993 | WIPO . |
| WO 93/16099 | 8/1993 | WIPO . |
| WO 94/01557 | 1/1994 | WIPO . |
| WO 94/15949 | 7/1994 | WIPO . |
| WO 94/15965 | 7/1994 | WIPO . |
| WO 94/15966 | 7/1994 | WIPO . |
| WO 94/21681 | 9/1994 | WIPO . |
| WO 94/26892 | 11/1994 | WIPO . |
| WO 94/26893 | 11/1994 | WIPO . |
| WO 95/01801 | 1/1995 | WIPO . |
| WO 95/01802 | 1/1995 | WIPO . |
| WO 95/10539 | 4/1995 | WIPO . |
| WO 95/16035 | 6/1995 | WIPO . |
| WO 96/01845 | 1/1996 | WIPO . |
| WO 96/02559 | 2/1996 | WIPO . |

OTHER PUBLICATIONS

DeRobertis and Sasai, Nature 380:37 (1996).
Sasai et al., Nature 376:333 (1995).
Sasai et al., Cell 79:779 (1994).
LaVallie et al., Bio/Technology 11:187 (1993).
Jing et al., Cell 85:1113 (1996).
Treanor et al., Nature 382:80 (1996).
Piccolo et al., Cell 86:589 (1996).
Jones et al., Mol. Endocrinol 6:1961 (1992).
Toyoshima et al., PNAS USA 90:5404 (1993).
Partanen et al., Mol. Cell Biol. 12:1698 (1992).
Crossier et al., Growth Factors 11:137 (1994).
Graham et al., Cell Growth and Differentiation 5:647 (1994).
Morris et al., Science 263:1281 (1994).
Masiakowski and Carroll, J. Biol. Chem. 267:26181 (1992).
Valenzuela et al., Neuron 15:573 (1995).
Tamagnone et al., Oncogene 8:2009 (1993).
Paul et al., Int. J. Cell Cloning 10:309 (1992).
Ganju et al., Oncogene 11:281 (1995).
Karn et al., Oncogene 8:3443 (1993).
Johnson et al., PNAS USA 90:5677 (1993).
Broxmeyer et al., PNAS USA 85:9052 (1988).
Eto et al., Biochem. Biophys. Res. Comm. 142:1095 (1987).
Matzuk et al., Nature 360:313 (1992).
Ogawa et al., J. Biol. Chem. 267:14233 (1992).
Thies et al., J. Bone & Min. Res. 5:305 (1990).
Thies et al., Endocrinology 130:1318 (1992).
Fukui et al., Developmental Biology 159:131 (1993).
Krummen et al., Endocrinology 132:431 (1993).
Vaughn and Vale, Endocrinology 132:2038 (1993).
Wozeney et al.., "Bone Morphogenetic Proteins", Chapter 20, In, Handbook of Experimental Pharmacology, vol. 107, *Physiology and Pharmacology of Bone* (eds., G.R. Mundy and T. J. Martin), pp. 725–748, Springer–Verlag, Heidelberg, 1993.
Celeste et al., Identification of transforming growth factor .beta. Family members present in bone–inductive protein purified from bovine bone. *Proc. Natl. Aacad. Sci,* U.S.A. (1990), 87(24), 9843–7.

*Primary Examiner*—Elizabeth Kemmerer
*Assistant Examiner*—David S. Romeo
*Attorney, Agent, or Firm*—Steven R. Lazar

[57] ABSTRACT

Purified chordin proteins and processes for producing them are disclosed. DNA molecules encoding the chordin proteins are also disclosed. The proteins may be used in the treatment of bone, cartilage, other connective tissue defects and disorders, including tendon, ligament and meniscus, in wound healing and related tissue repair, as well for treatment of disorders and defects to tissue which include epidermis, nerve, muscle, including cardiac muscle, and othe tissues and wounds, and organs such as liver, brain, lung, cardiac, pancreas and kidney tissue. The proteins may also be useful for the induction inhibition of growth and/or differentiation of undifferentiated embryonic and stem cells. The proteins may be complexed with other proteins, particularly members of the transforming growth factor-beta superfamily of proteins.

5 Claims, No Drawings

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 4425 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
GCGGCCGCCC GACGAGCCCC TCGCGGCACT GCCCCGGCCC CGGCCCCGGC CCCGGCCCCC      60

TCCCGCCGCA CCGCCCCCGG CCCGGCCCTC CGCCCTCCGC ACTCCCGCCT CCCTCCCTCC     120

GCCCGCTCCC GCGCCCTCCT CCCTCCCTCC TCCCCAGCTG TCCCGTTCGC GTCATGCCGA     180

GCCTCCCGGC CCCGCCGGCC CCGCTGCTGC TCCTCGGGCT GCTGCTGCTC GGCTCCCGGC     240

CGGCCCGCGG CGCCGGCCCC GAGCCCCCCG TGCTGCCCAT CCGTTCTGAG AAGGAGCCGC     300
```

```
TGCCCGTTCG GGGAGCGGCA GGCTGCACCT TCGGCGGGAA GGTCTATGCC TTGGACGAGA    360

CGTGGCACCC GGACCTAGGG GAGCCATTCG GGGTGATGCG CTGCGTGCTG TGCGCCTGCG    420

AGGCGACAGG GACCTTGAGG CCCAGAGAGA TGAAGTAGCT TGTCTAGGGT CACGCAGCTT    480

CCTCAGTGGG GTCGCCGTAC CAGGGGCCCT GGCAGGGTCA GCTGCAAGAA CATCAAACCA    540

GAGTGCCCAA CCCCGGCCTG TGGGCAGCCG CGCCAGCTGC CGGGACACTG CTGCCAGACC    600

TGCCCCCAGG AGCGCAGCAG TTCGGAGCGG CAGCCGAGCG GCCTGTCCTT CGAGTATCCG    660

CGGGACCCGG AGCATCGCAG TTATAGCGAC CGCGGGGAGC CAGGAGCTGA GGAGCGGGCC    720

CGTGGTGACG GCCACACGGA CTTCGTGGCG CTGCTGACAG GGCCGAGGTC GCAGGCGGTG    780

GCACGAGCCC GAGTCTCGCT GCTGCGCTCT AGCCTCCGCT TCTCTATCTC CTACAGGCGG    840

CTGGACCGCC CTACCAGGAT CCGCTTCTCA GACTCCAATG GCAGTGTCCT GTTTGAGCAC    900

CCTGCAGCCC CCACCCAAGA TGGCCTGGTC TGTGGGGTGT GGCGGGCAGT GCCTCGGTTG    960

TCTCTGCGGC TCCTTAGGGC AGAACAGCTG CATGTGGCAC TTGTGACACT CACTCACCCT   1020

TCAGGGGAGG TCTGGGGGCC TCTCATCCGG CACCGGGCCC TGGCTGCAGA GACCTTCAGT   1080

GCCATCCTGA CTCTAGAAGG CCCCCCACAG CAGGGCGTAG GGGGCATCAC CCTGCTCACT   1140

CTCAGTGACA CAGAGGACTC CTTGCATTTT TTGCTGCTCT TCCGAGGGCT GCTGGAACCC   1200

AGGAGTGGGG GACTAACCCA GGTTCCCTTG AGGCTCCAGA TTCTACACCA GGGGCAGCTA   1260

CTGCGAGAAC TTCAGGCCAA TGTCTCAGCC CAGGAACCAG GCTTTGCTGA GGTGCTGCCC   1320

AACCTGACAG TCCAGGAGAT GGACTGGCTG GTGCTGGGGG AGCTGCAGAT GGCCCTGGAG   1380

TGGGCAGGCA GGCCAGGGCT GCGCATCAGT GGACACATTG CTGCCAGGAA GAGCTGCGAC   1440

GTCCTGCAAA GTGTCCTTTG TGGGGCTGAT GCCCTGATCC CAGTCCAGAC GGGTGCTGCC   1500

GGCTCAGCCA GCCTCACGCT GCTAGGAAAT GGCTCCCTGA TCTATCAGGT GCAAGTGGTA   1560

GGGACAAGCA GTGAGGTGGT GGCCATGACA CTGGAGACCA AGCCTCAGCG GAGGGATCAG   1620

CGCACTGTCC TGTGCCACAT GGCTGGACTC CAGCCAGGAG GACACACGGC CGTGGGTATC   1680

TGCCCTGGGC TGGGTGCCCG AGGGGCTCAT ATGCTGCTGC AGAATGAGCT CTTCCTGAAC   1740

GTGGGCACCA AGGACTTCCC AGACGGAGAG CTTCGGGGGC ACGTGGCTGC CCTGCCCTAC   1800

TGTGGGCATA GCGCCCGCCA TGACACGCTG CCCGTGCCCC TAGCAGGAGC CCTGGTGCTA   1860

CCCCCTGTGA AGAGCCAAGC AGCAGGGCAC GCCTGGCTTT CCTTGGATAC CCACTGTCAC   1920

CTGCACTATG AAGTGCTGCT GGCTGGGCTT GGTGGCTCAG AACAAGGCAC TGTCACTGCC   1980

CACCTCCTTG GGCCTCCTGG AACGCCAGGG CCTCGGCGGC TGCTGAAGGG ATTCTATGGC   2040

TCAGAGGCCC AGGGTGTGGT GAAGGACCTG GAGCCGGAAC TGCTGCGGCA CCTGGCAAAA   2100

GGCATGGCCT CCCTGATGAT CACCACCAAG GGTAGCCCCA GAGGGGAGCT CCGAGGGCAG   2160

GTGCACATAG CCAACCAATG TGAGGTTGGC GGACTGCGCC TGGAGGCGGC CGGGGCCGAG   2220

GGGGTGCGGG CGCTGGGGGC TCCGGATACA GCCTCTGCTG CGCCGCCTGT GGTGCCTGGT   2280

CTCCCGGCCC TAGCGCCCGC CAAACCTGGT GGTCCTGGGC GGCCCCGAGA CCCCAACACA   2340

TGCTTCTTCG AGGGGCAGCA GCGCCCCCAC GGGGCTCGCT GGGCGCCCAA CTACGACCCG   2400

CTCTGCTCAC TCTGCACCTG CCAGAGACGA ACGGTGATCT GTGACCCGGT GGTGTGCCCA   2460

CCGCCCAGCT GCCCACACCC GGTGCAGGCT CCCGACCAGT GCTGCCCTGT TTGCCCTGAG   2520

AAACAAGATG TCAGAGACTT GCCAGGGCTG CCAAGGAGCC GGGACCCAGG AGAGGGCTGC   2580

TATTTTGATG GTGACCGGAG CTGGCGGGCA GCGGGTACGC GGTGGCACCC CGTTGTGCCC   2640

CCCTTTGGCT TAATTAAGTG TGCTGTCTGC ACCTGCAAGG GGGGCACTGG AGAGGTGCAC   2700
```

```
TGTGAGAAGG TGCAGTGTCC CCGGCTGGCC TGTGCCCAGC CTGTGCGTGT CAACCCCACC    2760

GACTGCTGCA AACAGTGTCC AGTGGGGTCG GGGGCCCACC CCCAGCTGGG GGACCCCATG    2820

CAGGCTGATG GCCCCGGGG CTGCCGTTTT GCTGGGCAGT GGTTCCCAGA GAGTCAGAGC     2880

TGGCACCCCT CAGTGCCCCC TTTTGGAGAG ATGAGCTGTA TCACCTGCAG ATGTGGGCA     2940

GGGGTGCCTC ACTGTGAGCG GGATGACTGT TCACTGCCAC TGTCCTGTGG CTCGGGGAAG    3000

GAGAGTCGAT GCTGTTCCCG CTGCACGGCC CACCGGCGGC CCCCAGAGAC CAGAACTGAT    3060

CCAGAGCTGG AGAAAGAAGC CGAAGGCTCT TAGGGAGCAG CCAGAGGGCC AAGTGACCAA    3120

GAGGATGGGG CCTGAGCTGG GGAAGGGGTG GCATCGAGGA CCTTCTTGCA TTCTCCTGTG    3180

GGAAGCCCAG TGCCTTTGCT CCTCTGTCCT GCCTCTACTC CCACCCCCAC TACCTCTGGG    3240

AACCACAGCT CCACAAGGGG GAGAGGCAGC TGGGCCAGAC CGAGGTCACA GCCACTCCAA    3300

GTCCTGCCCT GCCACCCTCG GCCTCTGTCC TGGAAGCCCC ACCCCTTTCC TCCTGTACAT    3360

AATGTCACTG GCTTGTTGGG ATTTTTAATT TATCTTCACT CAGCACCAAG GGCCCCCGAC    3420

ACTCCACTCC TGCTGCCCCT GAGCTGAGCA GAGTCATTAT TGGAGAGTTT TGTATTTATT    3480

AAAACATTTC TTTTTCAGTC AAAAAAAAAA AAAATCCCGA TTGTAACTAT TATGAGTCCT    3540

AGTTGACTTG AAGTGGAGAA GGCTACGATT TTTTTGATGT CATTTTGTGT AAGGGCGCAG    3600

ACTGCTGCGA ACAGAGTGGT GATAGCGCCT AAGCATAGTG TTAGAGTTTG GATTAGTGGG    3660

CTATTTTCTG CTAGGGGGTG GAAGCGGATG AGTAAGAAGA TTCCTGCTAC AACTATAGTG    3720

CTTGAGTGGA GTAGGGCTGA GACTGGGGTG GGGCCTTCTA TGGCTGAGGG GAGTCAGGGG    3780

TGGAGACCTA ATTGGGCTGA TTTGCCTGCT GCTGCTAGGA GGAGGCCTAG TAGTGGGGTG    3840

AGGCTTGGAT TAGCGTTTAG AAGGGCTATT TGTTGTGGGT CTCATGAGTT GGAGTGTAGG    3900

ATAAATCATG CTAAGGCGAG GATGAAACCG ATATCGCCGA TACGGTTGTA TAGGATTGCT    3960

TGAATGGCTG CTGTGTTGGC ATCTGCTCGG GCGTATCATC AACTGATGAG CAAGAAGGAT    4020

ATAATTCCTA CGCCCTCTCA GCCGATGAAC AGTTGGAATA GGTTGTTAGC GGTAACTAAG    4080

ATTAGTATGG TAATTAGGAA GATGAGTAGA TATTTGAAGA ACTGATTAAT GTTTGGGTCT    4140

GAGTTTATAT ATCACAGTGA GAATTCTATG ATGGACCATG TAACGAACAA TGCTACAGGG    4200

ATGAATATTA TGGAGAAGTA GTCTAGTTTG AAGCTTAGGG AGAGCTGGGT TGTTTGGGTT    4260

GTGGCTCAGT GTCAGTTCGA GATAATAACT TCTTGGTCTA GGCACATGAA TATTGTTGTG    4320

GGGAAGAGAC TGATAATAAA GGTGGATGCG ACAATGGATT TTACATAATG GGGTATGAG     4380

TTTTTTTTGT TAGGGTTAAC GAGGGTAGGC CTCTTTGGCC GAATT                    4425
```

(2) INFORMATION FOR SEQ ID NO:2:

(i) SEQUENCE CHARACTERISTICS:
        (A) LENGTH: 2865 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..2862

(xi) SEQUENCE DESCRIPTION: SEQ ID NO:2:

```
ATG CCG AGC CTC CCG GCC CCG CCG GCC CCG CTG CTG CTC CTC GGG CTG        48
Met Pro Ser Leu Pro Ala Pro Pro Ala Pro Leu Leu Leu Leu Gly Leu
 1               5                  10                  15

CTG CTG CTC GGC TCC CGG CCG GCC CGC GGC GCC GGC CCC GAG CCC CCC        96
```

```
                 Leu Leu Leu Gly Ser Arg Pro Ala Arg Gly Ala Gly Pro Glu Pro Pro
                             20                  25                  30

GTG CTG CCC ATC CGT TCT GAG AAG GAG CCG CTG CCC GTT CGG GGA GCG                144
Val Leu Pro Ile Arg Ser Glu Lys Glu Pro Leu Pro Val Arg Gly Ala
             35                  40                  45

GCA GGC TGC ACC TTC GGC GGG AAG GTC TAT GCC TTG GAC GAG ACG TGG                192
Ala Gly Cys Thr Phe Gly Gly Lys Val Tyr Ala Leu Asp Glu Thr Trp
 50                  55                  60

CAC CCG GAC CTA GGG GAG CCA TTC GGG GTG ATG CGC TGC GTG CTG TGC                240
His Pro Asp Leu Gly Glu Pro Phe Gly Val Met Arg Cys Val Leu Cys
 65                  70                  75                  80

GCC TGC GAG GCG CCT CAG TGG GGT CGC CGT ACC AGG GGC CCT GGC AGG                288
Ala Cys Glu Ala Pro Gln Trp Gly Arg Arg Thr Arg Gly Pro Gly Arg
                 85                  90                  95

GTC AGC TGC AAG AAC ATC AAA CCA GAG TGC CCA ACC CCG GCC TGT GGG                336
Val Ser Cys Lys Asn Ile Lys Pro Glu Cys Pro Thr Pro Ala Cys Gly
            100                 105                 110

CAG CCG CGC CAG CTG CCG GGA CAC TGC TGC CAG ACC TGC CCC CAG GAG                384
Gln Pro Arg Gln Leu Pro Gly His Cys Cys Gln Thr Cys Pro Gln Glu
            115                 120                 125

CGC AGC AGT TCG GAG CGG CAG CCG AGC GGC CTG TCC TTC GAG TAT CCG                432
Arg Ser Ser Ser Glu Arg Gln Pro Ser Gly Leu Ser Phe Glu Tyr Pro
130                 135                 140

CGG GAC CCG GAG CAT CGC AGT TAT AGC GAC CGC GGG GAG CCA GGA GCT                480
Arg Asp Pro Glu His Arg Ser Tyr Ser Asp Arg Gly Glu Pro Gly Ala
145                 150                 155                 160

GAG GAG CGG GCC CGT GGT GAC GGC CAC ACG GAC TTC GTG GCG CTG CTG                528
Glu Glu Arg Ala Arg Gly Asp Gly His Thr Asp Phe Val Ala Leu Leu
                165                 170                 175

ACA GGG CCG AGG TCG CAG GCG GTG GCA CGA GCC CGA GTC TCG CTG CTG                576
Thr Gly Pro Arg Ser Gln Ala Val Ala Arg Ala Arg Val Ser Leu Leu
            180                 185                 190

CGC TCT AGC CTC CGC TTC TCT ATC TCC TAC AGG CGG CTG GAC CGC CCT                624
Arg Ser Ser Leu Arg Phe Ser Ile Ser Tyr Arg Arg Leu Asp Arg Pro
            195                 200                 205

ACC AGG ATC CGC TTC TCA GAC TCC AAT GGC AGT GTC CTG TTT GAG CAC                672
Thr Arg Ile Arg Phe Ser Asp Ser Asn Gly Ser Val Leu Phe Glu His
210                 215                 220

CCT GCA GCC CCC ACC CAA GAT GGC CTG GTC TGT GGG GTG TGG CGG GCA                720
Pro Ala Ala Pro Thr Gln Asp Gly Leu Val Cys Gly Val Trp Arg Ala
225                 230                 235                 240

GTG CCT CGG TTG TCT CTG CGG CTC CTT AGG GCA GAA CAG CTG CAT GTG                768
Val Pro Arg Leu Ser Leu Arg Leu Leu Arg Ala Glu Gln Leu His Val
                245                 250                 255

GCA CTT GTG ACA CTC ACT CAC CCT TCA GGG GAG GTC TGG GGG CCT CTC                816
Ala Leu Val Thr Leu Thr His Pro Ser Gly Glu Val Trp Gly Pro Leu
            260                 265                 270

ATC CGG CAC CGG GCC CTG GCT GCA GAG ACC TTC AGT GCC ATC CTG ACT                864
Ile Arg His Arg Ala Leu Ala Ala Glu Thr Phe Ser Ala Ile Leu Thr
            275                 280                 285

CTA GAA GGC CCC CCA CAG CAG GGC GTA GGG GGC ATC ACC CTG CTC ACT                912
Leu Glu Gly Pro Pro Gln Gln Gly Val Gly Gly Ile Thr Leu Leu Thr
        290                 295                 300

CTC AGT GAC ACA GAG GAC TCC TTG CAT TTT TTG CTG CTC TTC CGA GGG                960
Leu Ser Asp Thr Glu Asp Ser Leu His Phe Leu Leu Leu Phe Arg Gly
305                 310                 315                 320

CTG CTG GAA CCC AGG AGT GGG GGA CTA ACC CAG GTT CCC TTG AGG CTC               1008
Leu Leu Glu Pro Arg Ser Gly Gly Leu Thr Gln Val Pro Leu Arg Leu
                325                 330                 335

CAG ATT CTA CAC CAG GGG CAG CTA CTG CGA GAA CTT CAG GCC AAT GTC               1056
```

```
                Gln Ile Leu His Gln Gly Gln Leu Leu Arg Glu Leu Gln Ala Asn Val
                            340                 345                 350

TCA GCC CAG GAA CCA GGC TTT GCT GAG GTG CTG CCC AAC CTG ACA GTC          1104
Ser Ala Gln Glu Pro Gly Phe Ala Glu Val Leu Pro Asn Leu Thr Val
            355                 360                 365

CAG GAG ATG GAC TGG CTG GTG CTG GGG GAG CTG CAG ATG GCC CTG GAG          1152
Gln Glu Met Asp Trp Leu Val Leu Gly Glu Leu Gln Met Ala Leu Glu
        370                 375                 380

TGG GCA GGC AGG CCA GGG CTG CGC ATC AGT GGA CAC ATT GCT GCC AGG          1200
Trp Ala Gly Arg Pro Gly Leu Arg Ile Ser Gly His Ile Ala Ala Arg
385                 390                 395                 400

AAG AGC TGC GAC GTC CTG CAA AGT GTC CTT TGT GGG GCT GAT GCC CTG          1248
Lys Ser Cys Asp Val Leu Gln Ser Val Leu Cys Gly Ala Asp Ala Leu
                405                 410                 415

ATC CCA GTC CAG ACG GGT GCT GCC GGC TCA GCC AGC CTC ACG CTG CTA          1296
Ile Pro Val Gln Thr Gly Ala Ala Gly Ser Ala Ser Leu Thr Leu Leu
            420                 425                 430

GGA AAT GGC TCC CTG ATC TAT CAG GTG CAA GTG GTA GGG ACA AGC AGT          1344
Gly Asn Gly Ser Leu Ile Tyr Gln Val Gln Val Val Gly Thr Ser Ser
        435                 440                 445

GAG GTG GTG GCC ATG ACA CTG GAG ACC AAG CCT CAG CGG AGG GAT CAG          1392
Glu Val Val Ala Met Thr Leu Glu Thr Lys Pro Gln Arg Arg Asp Gln
    450                 455                 460

CGC ACT GTC CTG TGC CAC ATG GCT GGA CTC CAG CCA GGA GGA CAC ACG          1440
Arg Thr Val Leu Cys His Met Ala Gly Leu Gln Pro Gly Gly His Thr
465                 470                 475                 480

GCC GTG GGT ATC TGC CCT GGG CTG GGT GCC CGA GGG GCT CAT ATG CTG          1488
Ala Val Gly Ile Cys Pro Gly Leu Gly Ala Arg Gly Ala His Met Leu
                485                 490                 495

CTG CAG AAT GAG CTC TTC CTG AAC GTG GGC ACC AAG GAC TTC CCA GAC          1536
Leu Gln Asn Glu Leu Phe Leu Asn Val Gly Thr Lys Asp Phe Pro Asp
            500                 505                 510

GGA GAG CTT CGG GGG CAC GTG GCT GCC CTG CCC TAC TGT GGG CAT AGC          1584
Gly Glu Leu Arg Gly His Val Ala Ala Leu Pro Tyr Cys Gly His Ser
        515                 520                 525

GCC CGC CAT GAC ACG CTG CCC GTG CCC CTA GCA GGA GCC CTG GTG CTA          1632
Ala Arg His Asp Thr Leu Pro Val Pro Leu Ala Gly Ala Leu Val Leu
    530                 535                 540

CCC CCT GTG AAG AGC CAA GCA GCA GGG CAC GCC TGG CTT TCC TTG GAT          1680
Pro Pro Val Lys Ser Gln Ala Ala Gly His Ala Trp Leu Ser Leu Asp
545                 550                 555                 560

ACC CAC TGT CAC CTG CAC TAT GAA GTG CTG CTG GCT GGG CTT GGT GGC          1728
Thr His Cys His Leu His Tyr Glu Val Leu Leu Ala Gly Leu Gly Gly
                565                 570                 575

TCA GAA CAA GGC ACT GTC ACT GCC CAC CTC CTT GGG CCT CCT GGA ACG          1776
Ser Glu Gln Gly Thr Val Thr Ala His Leu Leu Gly Pro Pro Gly Thr
            580                 585                 590

CCA GGG CCT CGG CGG CTG CTG AAG GGA TTC TAT GGC TCA GAG GCC CAG          1824
Pro Gly Pro Arg Arg Leu Leu Lys Gly Phe Tyr Gly Ser Glu Ala Gln
        595                 600                 605

GGT GTG GTG AAG GAC CTG GAG CCG GAA CTG CTG CGG CAC CTG GCA AAA          1872
Gly Val Val Lys Asp Leu Glu Pro Glu Leu Leu Arg His Leu Ala Lys
    610                 615                 620

GGC ATG GCC TCC CTG ATG ATC ACC ACC AAG GGT AGC CCC AGA GGG GAG          1920
Gly Met Ala Ser Leu Met Ile Thr Thr Lys Gly Ser Pro Arg Gly Glu
625                 630                 635                 640

CTC CGA GGG CAG GTG CAC ATA GCC AAC CAA TGT GAG GTT GGC GGA CTG          1968
Leu Arg Gly Gln Val His Ile Ala Asn Gln Cys Glu Val Gly Gly Leu
                645                 650                 655

CGC CTG GAG GCG GCC GGG GCC GAG GGG GTG CGG GCG CTG GGG GCT CCG          2016
```

-continued

```
                Arg Leu Glu Ala Ala Gly Ala Glu Gly Val Arg Ala Leu Gly Ala Pro
                                660                 665                 670

GAT ACA GCC TCT GCT GCG CCG CCT GTG GTG CCT GGT CTC CCG GCC CTA        2064
Asp Thr Ala Ser Ala Ala Pro Pro Val Val Pro Gly Leu Pro Ala Leu
                675                 680                 685

GCG CCC GCC AAA CCT GGT GGT CCT GGG CGG CCC CGA GAC CCC AAC ACA        2112
Ala Pro Ala Lys Pro Gly Gly Pro Gly Arg Pro Arg Asp Pro Asn Thr
    690                 695                 700

TGC TTC TTC GAG GGG CAG CAG CGC CCC CAC GGG GCT CGC TGG GCG CCC        2160
Cys Phe Phe Glu Gly Gln Gln Arg Pro His Gly Ala Arg Trp Ala Pro
705                 710                 715                 720

AAC TAC GAC CCG CTC TGC TCA CTC TGC ACC TGC CAG AGA CGA ACG GTG        2208
Asn Tyr Asp Pro Leu Cys Ser Leu Cys Thr Cys Gln Arg Arg Thr Val
                725                 730                 735

ATC TGT GAC CCG GTG GTG TGC CCA CCG CCC AGC TGC CCA CAC CCG GTG        2256
Ile Cys Asp Pro Val Val Cys Pro Pro Pro Ser Cys Pro His Pro Val
                740                 745                 750

CAG GCT CCC GAC CAG TGC TGC CCT GTT TGC CCT GAG AAA CAA GAT GTC        2304
Gln Ala Pro Asp Gln Cys Cys Pro Val Cys Pro Glu Lys Gln Asp Val
                755                 760                 765

AGA GAC TTG CCA GGG CTG CCA AGG AGC CGG GAC CCA GGA GAG GGC TGC        2352
Arg Asp Leu Pro Gly Leu Pro Arg Ser Arg Asp Pro Gly Glu Gly Cys
    770                 775                 780

TAT TTT GAT GGT GAC CGG AGC TGG CGG GCA GCG GGT ACG CGG TGG CAC        2400
Tyr Phe Asp Gly Asp Arg Ser Trp Arg Ala Ala Gly Thr Arg Trp His
785                 790                 795                 800

CCC GTT GTG CCC CCC TTT GGC TTA ATT AAG TGT GCT GTC TGC ACC TGC        2448
Pro Val Val Pro Pro Phe Gly Leu Ile Lys Cys Ala Val Cys Thr Cys
                805                 810                 815

AAG GGG GGC ACT GGA GAG GTG CAC TGT GAG AAG GTG CAG TGT CCC CGG        2496
Lys Gly Gly Thr Gly Glu Val His Cys Glu Lys Val Gln Cys Pro Arg
                820                 825                 830

CTG GCC TGT GCC CAG CCT GTG CGT GTC AAC CCC ACC GAC TGC TGC AAA        2544
Leu Ala Cys Ala Gln Pro Val Arg Val Asn Pro Thr Asp Cys Cys Lys
                835                 840                 845

CAG TGT CCA GTG GGG TCG GGG GCC CAC CCC CAG CTG GGG GAC CCC ATG        2592
Gln Cys Pro Val Gly Ser Gly Ala His Pro Gln Leu Gly Asp Pro Met
850                 855                 860

CAG GCT GAT GGG CCC CGG GGC TGC CGT TTT GCT GGG CAG TGG TTC CCA        2640
Gln Ala Asp Gly Pro Arg Gly Cys Arg Phe Ala Gly Gln Trp Phe Pro
865                 870                 875                 880

GAG AGT CAG AGC TGG CAC CCC TCA GTG CCC CCT TTT GGA GAG ATG AGC        2688
Glu Ser Gln Ser Trp His Pro Ser Val Pro Pro Phe Gly Glu Met Ser
                885                 890                 895

TGT ATC ACC TGC AGA TGT GGG GCA GGG GTG CCT CAC TGT GAG CGG GAT        2736
Cys Ile Thr Cys Arg Cys Gly Ala Gly Val Pro His Cys Glu Arg Asp
                900                 905                 910

GAC TGT TCA CTG CCA CTG TCC TGT GGC TCG GGG AAG GAG AGT CGA TGC        2784
Asp Cys Ser Leu Pro Leu Ser Cys Gly Ser Gly Lys Glu Ser Arg Cys
            915                 920                 925

TGT TCC CGC TGC ACG GCC CAC CGG CGG CCC CCA GAG ACC AGA ACT GAT        2832
Cys Ser Arg Cys Thr Ala His Arg Arg Pro Pro Glu Thr Arg Thr Asp
        930                 935                 940

CCA GAG CTG GAG AAA GAA GCC GAA GGC TCT TAG                            2865
Pro Glu Leu Glu Lys Glu Ala Glu Gly Ser
945                 950
```

(2) INFORMATION FOR SEQ ID NO:3:

(i) SEQUENCE CHARACTERISTICS:
        (A) LENGTH: 954 amino acids (B) TYPE: amino acid
        (D) TOPOLOGY: linear (ii) MOLECULE TYPE: protein (xi) SEQUENCE DESCRIPTION: SEQ ID NO:3:

```
Met Pro Ser Leu Pro Ala Pro Ala Pro Leu Leu Leu Gly Leu
1               5                  10                  15

Leu Leu Leu Gly Ser Arg Pro Ala Arg Gly Ala Gly Pro Glu Pro Pro
                20                  25                  30

Val Leu Pro Ile Arg Ser Glu Lys Glu Pro Leu Pro Val Arg Gly Ala
            35                  40                  45

Ala Gly Cys Thr Phe Gly Gly Lys Val Tyr Ala Leu Asp Glu Thr Trp
        50                  55                  60

His Pro Asp Leu Gly Glu Pro Phe Gly Val Met Arg Cys Val Leu Cys
65                  70                  75                  80

Ala Cys Glu Ala Pro Gln Trp Gly Arg Arg Thr Arg Gly Pro Gly Arg
                85                  90                  95

Val Ser Cys Lys Asn Ile Lys Pro Glu Cys Pro Thr Pro Ala Cys Gly
            100                 105                 110

Gln Pro Arg Gln Leu Pro Gly His Cys Cys Gln Thr Cys Pro Gln Glu
        115                 120                 125

Arg Ser Ser Glu Arg Gln Pro Ser Gly Leu Ser Phe Glu Tyr Pro
130                 135                 140

Arg Asp Pro Glu His Arg Ser Tyr Ser Asp Arg Gly Glu Pro Gly Ala
145                 150                 155                 160

Glu Glu Arg Ala Arg Gly Asp Gly His Thr Asp Phe Val Ala Leu Leu
                165                 170                 175

Thr Gly Pro Arg Ser Gln Ala Val Ala Arg Ala Arg Val Ser Leu Leu
            180                 185                 190

Arg Ser Ser Leu Arg Phe Ser Ile Ser Tyr Arg Arg Leu Asp Arg Pro
        195                 200                 205

Thr Arg Ile Arg Phe Ser Asp Ser Asn Gly Ser Val Leu Phe Glu His
210                 215                 220

Pro Ala Ala Pro Thr Gln Asp Gly Leu Val Cys Gly Val Trp Arg Ala
225                 230                 235                 240

Val Pro Arg Leu Ser Leu Arg Leu Leu Arg Ala Glu Gln Leu His Val
                245                 250                 255

Ala Leu Val Thr Leu Thr His Pro Ser Gly Glu Val Trp Gly Pro Leu
            260                 265                 270

Ile Arg His Arg Ala Leu Ala Ala Glu Thr Phe Ser Ala Ile Leu Thr
        275                 280                 285

Leu Glu Gly Pro Pro Gln Gln Gly Val Gly Gly Ile Thr Leu Leu Thr
290                 295                 300

Leu Ser Asp Thr Glu Asp Ser Leu His Phe Leu Leu Phe Arg Gly
305                 310                 315                 320

Leu Leu Glu Pro Arg Ser Gly Gly Leu Thr Gln Val Pro Leu Arg Leu
                325                 330                 335

Gln Ile Leu His Gln Gly Gln Leu Leu Arg Glu Leu Gln Ala Asn Val
            340                 345                 350

Ser Ala Gln Glu Pro Gly Phe Ala Glu Val Leu Pro Asn Leu Thr Val
        355                 360                 365

Gln Glu Met Asp Trp Leu Val Leu Gly Glu Leu Gln Met Ala Leu Glu
370                 375                 380

Trp Ala Gly Arg Pro Gly Leu Arg Ile Ser Gly His Ile Ala Ala Arg
```

-continued

```
385                 390                 395                 400
Lys Ser Cys Asp Val Leu Gln Ser Val Leu Cys Gly Ala Asp Ala Leu
                405                 410                 415
Ile Pro Val Gln Thr Gly Ala Ala Gly Ser Ala Ser Leu Thr Leu Leu
                420                 425                 430
Gly Asn Gly Ser Leu Ile Tyr Gln Val Gln Val Val Gly Thr Ser Ser
                435                 440                 445
Glu Val Val Ala Met Thr Leu Glu Thr Lys Pro Gln Arg Arg Asp Gln
        450                 455                 460
Arg Thr Val Leu Cys His Met Ala Gly Leu Gln Pro Gly Gly His Thr
465                 470                 475                 480
Ala Val Gly Ile Cys Pro Gly Leu Gly Ala Arg Gly Ala His Met Leu
                485                 490                 495
Leu Gln Asn Glu Leu Phe Leu Asn Val Gly Thr Lys Asp Phe Pro Asp
                500                 505                 510
Gly Glu Leu Arg Gly His Val Ala Ala Leu Pro Tyr Cys Gly His Ser
                515                 520                 525
Ala Arg His Asp Thr Leu Pro Val Pro Leu Ala Gly Ala Leu Val Leu
        530                 535                 540
Pro Pro Val Lys Ser Gln Ala Ala Gly His Ala Trp Leu Ser Leu Asp
545                 550                 555                 560
Thr His Cys His Leu His Tyr Glu Val Leu Leu Ala Gly Leu Gly Gly
                565                 570                 575
Ser Glu Gln Gly Thr Val Thr Ala His Leu Leu Gly Pro Pro Gly Thr
                580                 585                 590
Pro Gly Pro Arg Arg Leu Leu Lys Gly Phe Tyr Gly Ser Glu Ala Gln
                595                 600                 605
Gly Val Val Lys Asp Leu Glu Pro Glu Leu Leu Arg His Leu Ala Lys
        610                 615                 620
Gly Met Ala Ser Leu Met Ile Thr Thr Lys Gly Ser Pro Arg Gly Glu
625                 630                 635                 640
Leu Arg Gly Gln Val His Ile Ala Asn Gln Cys Glu Val Gly Gly Leu
                645                 650                 655
Arg Leu Glu Ala Ala Gly Ala Glu Gly Val Arg Ala Leu Gly Ala Pro
                660                 665                 670
Asp Thr Ala Ser Ala Ala Pro Val Val Pro Gly Leu Pro Ala Leu
        675                 680                 685
Ala Pro Ala Lys Pro Gly Gly Pro Gly Arg Pro Arg Asp Pro Asn Thr
        690                 695                 700
Cys Phe Phe Glu Gly Gln Gln Arg Pro His Gly Ala Arg Trp Ala Pro
705                 710                 715                 720
Asn Tyr Asp Pro Leu Cys Ser Leu Cys Thr Cys Gln Arg Arg Thr Val
                725                 730                 735
Ile Cys Asp Pro Val Val Cys Pro Pro Pro Ser Cys Pro His Pro Val
                740                 745                 750
Gln Ala Pro Asp Gln Cys Cys Pro Val Cys Pro Glu Lys Gln Asp Val
                755                 760                 765
Arg Asp Leu Pro Gly Leu Pro Arg Ser Arg Asp Pro Gly Glu Gly Cys
        770                 775                 780
Tyr Phe Asp Gly Asp Arg Ser Trp Arg Ala Ala Gly Thr Arg Trp His
785                 790                 795                 800
Pro Val Val Pro Pro Phe Gly Leu Ile Lys Cys Ala Val Cys Thr Cys
                805                 810                 815
```

```
Lys Gly Gly Thr Gly Glu Val His Cys Glu Lys Val Gln Cys Pro Arg
            820                 825                 830

Leu Ala Cys Ala Gln Pro Val Arg Val Asn Pro Thr Asp Cys Cys Lys
            835                 840                 845

Gln Cys Pro Val Gly Ser Gly Ala His Pro Gln Leu Gly Asp Pro Met
850                 855                 860

Gln Ala Asp Gly Pro Arg Gly Cys Arg Phe Ala Gly Gln Trp Phe Pro
865                 870                 875                 880

Glu Ser Gln Ser Trp His Pro Ser Val Pro Pro Phe Gly Glu Met Ser
                885                 890                 895

Cys Ile Thr Cys Arg Cys Gly Ala Gly Val Pro His Cys Glu Arg Asp
            900                 905                 910

Asp Cys Ser Leu Pro Leu Ser Cys Gly Ser Gly Lys Glu Ser Arg Cys
            915                 920                 925

Cys Ser Arg Cys Thr Ala His Arg Arg Pro Pro Glu Thr Arg Thr Asp
            930                 935                 940

Pro Glu Leu Glu Lys Glu Ala Glu Gly Ser
945                 950
```

(2) INFORMATION FOR SEQ ID NO:4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CCACGTCTCG TCCAAGGCAT AGACCTT                                           27

(2) INFORMATION FOR SEQ ID NO:5:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CATGGGCAGC TCGAG                                                            15

(2) INFORMATION FOR SEQ ID NO:6:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CTGCAGGCGA GCCTGAATTC CTCGAGCCAT CATG                                 34

(2) INFORMATION FOR SEQ ID NO:7:

(i) SEQUENCE CHARACTERISTICS:
        (A) LENGTH: 83 base pairs
        (B) TYPE: nucleic acid
        (C) STRANDEDNESS: single
        (D) TOPOLOGY: linear -continued (ii) MOLECULE TYPE: DNA (genomic)

(xi) SEQUENCE DESCRIPTION: SEQ ID NO:7:

```
CCCCTGTGGG TAGAACGAGG TTAAAAAACG TCTAGGCCCC CCGAACCACG GGGACGTGGT    60

TTTCCTTTGA AAAACACGAT TGC                                           83
```

CHORDIN COMPOSITIONS

This application is a divisional of U.S. Ser. No. 08/749,169, U.S. Pat. No. 5,846,770 filed Nov. 14, 1996, which application is a continuation-in-part of U.S. Ser. No. 08/343,760, filed Nov. 22, 1994, and now issued as U.S. Pat. No. 5,679,783.

The present invention relates to a novel family of purified proteins designated chordin and related proteins, DNA encoding them, and processes for obtaining them. These proteins may be used to induce and/or regulate bone and/or cartilage or other connective tissue formation, and in wound healing and tissue repair. These proteins may also be used for augmenting the activity of other bone morphogenetic proteins.

BACKGROUND OF THE INVENTION

The search for the molecule or molecules responsible for the bone-, cartilage-, and other connective tissue-inductive activity present in bone and other tissue extracts has led to the discovery and identification of a several groups of molecules, such as the Bone Morphogenetic Proteins (BMPs). The unique inductive activities of these proteins, along with their presence in bone, suggests that they are important regulators of bone repair processes, and may be involved in the normal maintenance of bone tissue. There is a need to identify whether additional proteins, particularly human proteins, exist which play a role in these processes. It has recently been reported that *Xenopus chordin* is a molecule which contributes to dorsoventral patterning by binding to BMP-4. Piccolo et al., *Cell*, 86:589–98 (1996). The present invention relates to the identification of such a novel human protein, which the inventors have designated human *chordin*.

Human chordin is the human homolog of a xenopus protein called chordin. The nucleotide and amino acid sequences of *xenopus chordin* are described in Lasai et al., *Cell*, 79:779–790 (1994). The *xenopus chordin* gene has been described as being expressed in the frog embryo head, trunk and tail organizer regions during gastrulation, and as being capable of inducing secondary axes in frog embryos, and rescuing axis formation in ventralized frog, as well as modifying mesoderm induction. Ibid. In addition, *xenopus chordin* has been shown to induce anterior neural markers in the absence of mesoderm induction. Sashai et al., *Nature*, 376:333–336 (1995).

SUMMARY OF THE INVENTION

As used herein, the term chordin protein refers to the human chordin protein, having the amino acid sequence specified in SEQUENCE ID NO: 2, as well as DNA sequences encoding the chordin protein, such as the native human sequence shown in SEQUENCE ID NO: 1. Also included are naturally occurring allelic sequences and synthetic variants of SEQUENCE ID NO: 1 and 2, and equivalent degenerative codon sequences of the above.

The chordin DNA sequence (SEQ ID NO: 1) and amino acid sequence (SEQ ID NO: 2) are set forth in the Sequence Listings. Chordin proteins may be capable of binding to BMPs and/or inducing or altering the formation of cartilage, bone, or other connective tissue, or combinations thereof. Thus, chordin proteins may be assayed using BMP binding assays, as described in the examples, as well as the cartilage and bone formation and other assays described below. Chordin proteins may be further characterized by the ability to demonstrate effects upon the growth and/or differentiation of embryonic cells and/or stem cells. Thus, the proteins or compositions of the present invention may also be useful for treating cell populations, such as embryonic cells or stem cell populations, to enhance or enrich the growth and/or differentiation of the cells.

Human chordin protein may be produced by culturing a cell transformed with a DNA sequence comprising nucleotides encoding the mature chordin polypeptide and, in the case of eukaryotic cells, a suitable signal peptide. Such DNA sequences, for example, may comprise nucleotide #1 to nucleotide #4425 as shown in SEQ ID NO: 1, or nucleotide #1, 64, 70 or 79 to #2862 as shown in SEQ ID NO: 2. The protein may be recovered and purified from the culture medium from such transformed cells. Such protein may be characterized by an amino acid sequence comprising amino acids #1, 22, 24 or 27 to #954 as shown in SEQ ID NO: 3 substantially free from other proteinaceous materials with which it is co-produced. For production in mammalian cells, the DNA sequence further comprises a DNA sequence encoding a suitable propeptide 5' to and linked in frame to the nucleotide sequence encoding the mature chordin-related polypeptide. The propeptide may be the native chordin-related propeptide, or may be a propeptide from another protein of a related protein. Where the native chordin propeptide is used, human chordin may be produced by culturing a cell transformed with a DNA sequence comprising a DNA sequence encoding the full chordin polypeptide, comprising nucleotide #1 to #2862 as shown in SEQ ID NO: 2 producing a protein characterized by the amino acid sequence comprising amino acids #1 to #954 as shown in SEQ ID NO: 3. of which amino acids 1 to 23 comprise the native propeptide of human chordin, and recovering and purifying from the culture medium a protein characterized by the amino acid sequence comprising amino acids #24 to #954 as shown in SEQ ID NO: 3, substantially free from other proteinaceous materials with which it is co-produced. It is possible that chordin, as produced in nature, may be a heterologous mixture of proteins with varying N-termini. Potential N-termini of the mature protein include amino acid 22, 24 and 27. Thus, the DNA encoding chordin beginning with nucleotides encoding each of these amino acid residues, and the corresponding peptide sequences, are included in the present invention.

It is expected that other species, particularly human, have DNA sequences homologous to human chordin protein. The invention, therefore, includes methods for obtaining the DNA sequences encoding human chordin protein, the DNA sequences obtained by those methods, and the human protein encoded by those DNA sequences. This method entails utilizing the human chordin protein nucleotide sequence or portions thereof to design probes to screen libraries for the corresponding gene from other species or coding sequences or fragments thereof from using standard techniques. Thus, the present invention may include DNA sequences from other species, which are homologous to human chordin protein and can be obtained using the human chordin sequence. The present invention may also include functional fragments of the human chordin protein, and DNA sequences encoding such functional fragments, as well as functional fragments of other related proteins. The ability of such a fragment to function is determinable by assay of the protein in the biological assays described for the assay of the chordin protein; for example the BMP binding assays described in the examples. A DNA sequence encoding the complete mature human chordin protein (SEQ ID NO: 1 and SEQ ID NO: 2) and the corresponding amino acid sequence (SEQ ID NO: 3) are set forth herein. The chordin proteins of the present invention, such as human chordin, may be produced by culturing a cell transformed with the correlating DNA sequence, such as the human chordin DNA sequence of SEQ ID NO: 2, and recovering and purifying protein, such as human chordin, from the culture medium. The purified expressed protein is substantially free from other proteinaceous materials with which it is co-produced, as well as from other contaminants. The recovered purified protein is contemplated to have the ability to bind to BMPs and hence to exhibit effects on cartilage, bone and/or other connective tissue formation activity. Thus, the proteins of the invention may be further characterized by the ability to demonstrate effects on cartilage, bone and/or other connective tissue formation activity in bone and cartilage formation and other assays described below. Chordin proteins may be further characterized by the ability to demonstrate effects upon the growth and/or differentiation of embryonic cells and/or stem cells. Thus, the proteins or compositions of the present invention may also be characterized by their ability to enhance, enrich or otherwise influence the growth and/or differentiation of the cells.

Another aspect of the invention provides pharmaceutical compositions containing a therapeutically effective amount of human chordin protein, in a pharmaceutically acceptable vehicle or carrier. These compositions of the invention may be used in regulating the formation of bone, cartilage, or other connective tissue, including tendon, ligament, meniscus and other connective tissue, as well as combinations of the above, for example, for regeneration of the tendon-to-bone attachment apparatus. In addition, the compositions of the present invention may be useful for the induction, growth, differentiation, maintenance and/or repair of tissues such as brain, liver, kidney, lung, heart, muscle, epidermis, pancreas, nerve, and other organs. The compositions of the present invention, such as compositions of human chordin, may also be used for wound healing and organ and tissue growth and repair (for example, for ex vivo culture of cells and/or organ cultures).

Compositions of the invention may further include at least one other therapeutically useful agent such as members of the TGF-β superfamily of proteins, which includes BMP proteins BMP-1, BMP-2, BMP-3, BMP-4, BMP-5, BMP-6 and BMP-7, disclosed for instance in U.S. Pat. Nos. 5,108, 922; 5,013,649; 5,116,738; 5,106,748; 5,187,076; and 5,141, 905; BMP-8, disclosed in PCT publication WO91/18098; and BMP-9, disclosed in PCT publication WO93/00432, BMP-10, disclosed in PCT application WO94/26893; BMP-11, disclosed in PCT application WO94/26892, or BMP-12 or BMP-13, disclosed in PCT application WO95/16035; BMP-15, disclosed in co-pending patent application, serial no. 08/446,924, filed on May 18, 1995; or BMP-16, disclosed in co-pending patent application, Ser. No. 08/715, 202, filed on Sep. 18, 1996. Other compositions which may also be useful include Vgr-2, Jones et al., *Mol Endocrinol*, 6:1961–1968 (1992), and any of the growth and differentiation factors [GDFs], including those described in PCT applications WO94/15965; WO94/15949; WO95/01801; WO95/01802; WO94/21681; WO94/15966; WO95/10539; WO96/01845; WO96/02559 and others. Also useful in the present invention may be BIP, disclosed in WO94/01557; HP00269, disclosed in JP Publication number: 7-250688; and MP52. disclosed in PCT application WO93/16099. The disclosures of all of the above applications are hereby incorporated by reference.

It is postulated that chordin's effects may be mediated by interaction with other molecules, such as the TGF-β proteins described above, and may interact with one or more receptor molecules, such as the tyrosine kinase receptors. Thus, the composition of the present invention may comprise a complex comprised of the chordin-related protein of the present invention with one or more other molecules, such as the TGF-β proteins described above. Thus, the present invention includes complexes of chordin polypeptide with at least one polypeptide subunit from a transforming growth factor-beta [TGF-β] superfamily protein member. Further, tyrosine kinase receptor genes and/or proteins, and/or soluble truncated versions thereof, may also be useful in compositions of the present invention, including the following receptors, or soluble truncated versions comprising the extracellular binding domains thereof: LTK, Toyoshima et al., *PNAS USA* 90:5404 (1993); TIE, Partanen et al., *Mol. Cell Biol* 12:1698 (1992); DTK, Crosier et al., *Growth Factors* 11:137 (1994); MER, Graham et al., *Cell Growth and Differentiation* 5:647 (1994); ALK, Morris et al., *Science* 263:1281 (1994); RYK, Tamagnone et al., *Oncogene* 8:2009 (1993); Paul et al., *Int. J Cell Cloning* 10:309 (1992); ROR1 and ROR2, Masiakowski and Carroll, *J. Biol. Chem.* 267:26181 (1992); MuSK/Mlk/Nsk2, Valenzuela et al., *Neuron* 15:573 (1995); Ganju et al., *Oncogene* 11:281 (1995); TKT, Karn et al., *Oncogene* 8:3443 (1993); and DDR, Johnson et al., *PNAS USA* 90:5677 (1993). The disclosure of the above references is hereby incorporated by reference as if reproduced fully herein.

The compositions of the invention may comprise, in addition to a chordin-related protein, other therapeutically useful agents including growth factors such as epidermal growth factor (EGF), fibroblast growth factor (FGF), transforming growth factor (TGF-α and TGF-β), activins, inhibins, and insulin-like growth factor (IGF). The compositions may also include an appropriate matrix for instance, for supporting the composition and providing a surface for bone and/or cartilage and/or other connective tissue growth. The matrix may provide slow release of the osteoinductive protein and/or the appropriate environment for presentation thereof.

The chordin containing compositions may be employed in methods for treating a number of bone and/or cartilage and/or other connective tissue defects, periodontal disease and healing of various types of tissues and wounds. The tissue and wounds which may be treated include epidermis, nerve, muscle, including cardiac muscle, and other tissues and wounds, and other organs such as liver, brain, lung, cardiac, pancreas and kidney tissue. These methods, according to the invention, entail administering to a patient needing bone, cartilage and/or other connective tissue formation, wound healing or tissue repair, an effective amount of a composition comprising chordin protein. The chordin-containing compositions may also be used to treat or prevent such conditions as osteoarthritis. osteoporosis, and other abnormalities of bone, cartilage, muscle, tendon, ligament or other connective tissue, organs such as liver, brain, lung, cardiac, pancreas and kidney tissue, and other tissues. These methods may also entail the administration of a protein of the invention in conjunction with at least one BMP protein or other growth factor as described above. In addition, these methods may also include the administration of a chordin protein with other growth factors including EGF, FGF, TGF-α, TGF-β, activin, inhibin and IGF.

Still a further aspect of the invention are DNA sequences coding for expression of a chordin protein. Such sequences include the sequence of nucleotides in a 5' to 3' direction illustrated in SEQ ID NO: 1 or SEQ ID NO: 2, DNA sequences which, but for the degeneracy of the genetic code, are identical to the DNA sequence SEQ ID NO: 1 or SEQ ID NO: 2, and DNA sequences which encode the protein of SEQ ID NO: 3. Further included in the present invention are DNA sequences which hybridize under stringent conditions with the DNA sequence of SEQ ID NO: 1 or SEQ ID NO: 2 and encode a protein having the ability to influence the formation of cartilage and/or bone and/or other connective tissue, or other organs such as liver, brain, lung, cardiac, pancreas and kidney tissue. Preferred DNA sequences include those which hybridize under stringent conditions [see, T. Maniatis et al, *Molecular Cloning (A Laboratory Manual)*, Cold Spring Harbor Laboratory (1982), pages 387 to 3891. It is generally preferred that such DNA sequences encode a polypeptide which is at least about 80% homologous, and more preferably at least about 90% homologous, to the mature human chordin amino acid sequence shown in SEQ ID NO: 1 or SEQ ID NO: 2. Finally, allelic or other variations of the sequences of SEQ ID NO: 1 or SEQ ID NO: 2, whether such nucleotide changes result in changes in the peptide sequence or not, but where the peptide sequence still has chordin activity, are also included in the present invention. The present invention also includes fragments of the DNA sequence of chordin shown in SEQ ID NO: 1 or SEQ ID NO: 2 which encode a polypeptide which retains the activity of chordin protein.

The DNA sequences of the present invention are useful, for example, as probes for the detection of mRNA encoding chordin in a given cell population. Thus, the present invention includes methods of detecting or diagnosing genetic disorders involving the chordin gene, or disorders involving cellular, organ or tissue disorders in which chordin is irregularly transcribed or expressed. The DNA sequences may also be useful for preparing vectors for gene therapy applications as described below.

A further aspect of the invention includes vectors comprising a DNA sequence as described above in operative association with an expression control sequence therefor. These vectors may be employed in a novel process for producing a chordin protein of the invention in which a cell line transformed with a DNA sequence encoding a chordin protein in operative association with an expression control sequence therefor, is cultured in a suitable culture medium and a chordin-related protein is recovered and purified therefrom. This process may employ a number of known cells both prokaryotic and eukaryotic as host cells for expression of the polypeptide. The vectors may be used in gene therapy applications. In such use, the vectors may be transfected into the cells of a patient ex vivo, and the cells may be reintroduced into a patient. Alternatively, the vectors may be introduced into a patient in vivo through targeted transfection.

Still a further aspect of the invention are chordin proteins or polypeptides. Such polypeptides are characterized by having an amino acid sequence including the sequence illustrated in SEQ ID NO: 3, variants of the amino acid sequence of SEQ ID NO: 3, including naturally occurring allelic variants, and other variants in which the protein retains the ability to bind to BMPs, and/or the ability to induce, inhibit or influence the formation of cartilage and/or bone and/or other connective tissue, or other organs such as liver, brain, lung, cardiac, pancreas and kidney tissue, or other activity characteristic of chordin. Preferred polypeptides include a polypeptide which is at least about 80% homologous, and more preferably at least about 90% homologous, to the mature human chordin amino acid sequence shown in SEQ ID NO: 3. Finally, allelic or other variations of the sequences of SEQ ID NO: 3, whether such amino acid changes are induced by mutagenesis, chemical alteration, or by alteration of DNA sequence used to produce the polypeptide, where the peptide sequence still retains chordin activity, as described in the Examples below, are also included in the present invention. The present invention also includes fragments of the amino acid sequence of chordin shown in SEQ ID NO: 3 which retain the activity of chordin protein, such as the ability to bind to BMPs.

The purified proteins of the present inventions may be used to generate antibodies, either monoclonal or polyclonal, to human chordin and/or other chordin-related proteins, using methods that are known in the art of antibody production. Thus, the present invention also includes antibodies to human chordin and/or other related proteins. The antibodies may be useful for purification of chordin and/or other chordin related proteins, or for inhibiting or preventing the effects of chordin related proteins, or may have agonist effects on cells with BMP receptors. The chordin protein and related proteins may be useful for inducing the growth and/or differentiation of embryonic cells and/or stem cells. Thus, the proteins or compositions of the present invention may also be useful for treating relatively undifferentiated cell populations, such as embryonic cells or stem cell populations, to enhance or enrich the growth and/or differentiation of the cells. The treated cell populations may be useful for implantation and for gene therapy applications.

Description of the Sequences

SEQ ID NO: 1 is a nucleotide sequence containing nucleotide sequence encoding the entire mature human chordin polypeptide. This sequence contains an intron which is not naturally translated into protein.

SEQ ID NO: 2 is a nucleotide sequence of human chordin which has been synthetically altered to enhance expression.

SEQ ID NO: 3 is the amino acid sequence containing the mature human chordin polypeptide sequence.

DETAILED DESCRIPTION OF THE INVENTION

The human chordin sequence of the present invention is obtained using the whole or fragments of the *xenopus chordin* DNA sequence, or a partial human chordin sequence, as a probe. Thus, the human chordin DNA sequence comprise the DNA sequence of nucleotides #1 to #4425 of SEQ ID NO: 1. This sequence of the human chordin DNA sequence corresponds well to the *xenopus chordin* DNA sequence described in GenBank accession number L35764. The human chordin protein comprises the sequence of amino acids #1 to 954 of SEQ ID NO: 3. The mature human chordin protein is encoded by nucleotides #70 to #2862 of SEQ ID NO: 1, and comprises the sequence of amino acids #24 to #954 of SEQ ID NO: 2. Other active species of human chordin are encoded by nucleotides #1, 64, 70 and 79 to #2862 of SEQ ID NO: 2, and comprise amino acids #1, 22, 24 or 27 to #954 of SEQ ID NO: 3.

It is expected that human chordin protein, as expressed by mammalian cells such as CHO cells, exists as a heterogeneous population of active species of chordin protein with varying N-termini. It is expected that active species will comprise an amino acid sequence beginning with the alanine residue at amino acid #27 of SEQ ID NO: 3, or will comprise additional amino acid sequence further in the N-terminal direction. Thus, it is expected that DNA sequences encoding active chordin proteins will comprise a nucleotide sequence comprising nucleotides #1, 64, 70, or 79 to #2862 of SEQ ID NO: 2. Accordingly, active species of human chordin are expected to include those comprising amino acids #1, 22, 24 or 27 to #954 of SEQ ID NO: 3.

A host cell may be transformed with a coding sequence encoding a propeptide suitable for the secretion of proteins by the host cell linked in proper reading frame to the coding sequence for the mature chordin protein. For example, see U.S. Pat. No. 5,168,050, in which a DNA encoding a precursor portion of a mammalian protein other than BMP-2 is fused to the DNA encoding a mature BMP-2 protein. See also the specification of WO95/16035, in which the propeptide of BMP-2 is fused to the DNA encodina a mature BMP-12 protein. The disclosure of both of these references are hereby incorporated by reference. Thus, the present invention includes chimeric DNA molecules comprising a DNA sequence encoding a propeptide from a protein, other than human chordin, such as a member of the TGF-β superfamily of proteins, linked in correct reading frame to a DNA sequence encoding human chordin protein, or a related protein. The term "chimeric" is used to signify that the propeptide originates from a different polypeptide than the chordin protein.

The N-terminus of one active species of human chordin is expected to be produced by expression in *E. coli* to be as follows: [M]ARGAGP corresponding to amino acids 24 to 29 of SEQ ID NO: 2. Thus, it appears that the N-terminus of this species of chordin is at amino acid #24 of SEQ ID NO: 3, and a DNA sequence encoding said species of chordin would comprise nucleotides #70 to #2862 of SEQ ID NO: 2. The apparent molecular weight of human chordin monomer is expected to be experimentally determined by SDS-PAGE to be approximately 105–110 kd on a Novex 10% tricine gel.

It is expected that other chordin proteins, as expressed by mammalian cells such as CHO cells, also exist as a heterogeneous population of active species of chordin-related protein with varying N-termini. For example, it is expected that active species of human chordin protein will comprise an amino acid sequence beginning with the alanine residue at amino acid #27 of SEQ ID NO: 3, or will comprise additional amino acid sequence further in the N-terminal direction. Thus, it is expected that DNA sequences encoding active chordin proteins include those which comprise a nucleotide sequence comprising nucleotides #1, # 64, # 70 or # 79 to #2862 of SEQ ID NO: 2. Accordingly, active human chordin proteins include those comprising amino acids #1, #22, #24 or #27 to #954 of SEQ ID NO: 3, as well as fragments of chordin [such as SEQ 3] which retain chordin activity.

The chordin proteins of the present invention, include polypeptides having a molecular weight of about 105–110 kd, said polypeptide comprising the amino acid sequence of SEQ ID NO: 3 and having the ability to bind to TGF-β and/or BMP proteins, or the ability to alter or influence the formation of cartilage and/or bone and/or other connective tissues, such as exhibited in the embryonic stem cell and Rosen-Modified Sampath-Reddi ectopic implant assays, described in the examples.

The chordin proteins recovered from the culture medium are purified by isolating them from other proteinaceous materials from which they are co-produced and from other contaminants present. Chordin proteins may be characterized by the ability to induce or otherwise influence the formation of cartilage and/or bone and/or other connective tissue and other tissue repair and differentiation, for example, in the embryonic stem cell assay and bone and cartilage formation and other assays, described in the examples below. In addition, chordin proteins may be further characterized by their effects upon the growth and/or differentiation of embryonic cells and/or stem cells. Thus, the proteins or compositions of the present invention may be characterized by the embryonic stem cell assay described below.

The chordin proteins provided herein also include factors encoded by the sequences similar to those of SEQ ID NO: 1 or SEQ ID NO: 2, but into which modifications or deletions are naturally provided (e.g. allelic variations in the nucleotide sequence which may result in amino acid changes in the polypeptide) or deliberately engineered. For example, synthetic polypeptides may wholly or partially duplicate continuous sequences of the amino acid residues of SEQ ID NO: 3. These sequences, by virtue of sharing primary, secondary, or tertiary structural and conformational characteristics with bone growth factor polypeptides of SEQ ID NO: 3 may possess biological properties in common therewith. It is know, for example that numerous conservative amino acid substitutions are possible without significantly modifying the structure and conformation of a protein, thus maintaining the biological properties as well. For example, it is recognized that conservative amino acid substitutions may be made among amino acids with basic side chains, such as lysine (Lys or K), arginine (Arg or R). and histidine (His or H); amino acids with acidic side chains, such as aspartic acid (Asp or D)) and glutamic acid (Glu or E); amino acids with uncharged polar side chains, such as asparagine (Asn or N), glutamine (Gln or Q), serine (Ser or S), threonine (Thr or T), and tyrosine (Tyr or Y); and amino acids with nonpolar side chains, such as alanine (Ala or A), glycine (Gly or G), valine (Val or V), leucine (Leu or L), isoleucine (Ile or I), proline (Pro or P), phenylalanine (Phe or F). methionine (Met or M), tryptophan (Trp or W) and cysteine (Cys or C). Thus, these modifications and deletions of the native chordin may be employed as biologically active substitutes for naturally-occurring chordin and other polypeptides in therapeutic processes. It can be readily determined whether a given variant of chordin maintains the biological activity of chordin by subjecting both chordin and the variant of chordin to the assays described in the examples.

Other specific mutations of the sequences of chordin proteins described herein involve modifications of glycosylation sites. These modifications may involve O-linked or N-linked glycosylation sites. For instance, the absence of glycosylation or only partial glycosylation results from amino acid substitution or deletion at asparagine-linked glycosylation recognition sites. The asparagine-linked glycosylation recognition sites comprise tripeptide sequences which are specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence. Additionally, bacterial expression of chordin-related protein will also result in production of a non-glycosylated protein, even if the glycosylation sites are left unmodified.

The present invention also encompasses the novel DNA sequences, free of association with DNA sequences encoding other proteinaceous materials, and coding for expression of chordin proteins. These DNA sequences include those depicted in SEQ ID NO: 1 in a 5' to 3' direction and those sequences which hybridize thereto under stringent hybridization washing conditions [for example, 0.1× SSC, 0.1% SDS at 65° C.; see, T. Maniatis et al, *Molecular Cloning (A Laboratory Manual)*, Cold Spring Harbor Laboratory (1982), pages 387 to 389] and encode a protein having cartilage and/or bone and/or other connective tissue inducing activity. These DNA sequences also include those which comprise the DNA sequence of SEQ ID NO: 1 or SEQ ID NO: 2 and those which hybridize thereto under stringent hybridization conditions and encode a protein which maintain the other activities disclosed for chordin.

Similarly, DNA sequences which code for chordin proteins coded for by the sequences of SEQ ID NO: 1 or SEQ ID NO: 2, or chordin proteins which comprise the amino acid sequence of SEQ ID NO: 3, but which differ in codon sequence due to the degeneracies of the genetic code or allelic variations (naturally-occurring base changes in the species population which may or may not result in an amino acid change) also encode the novel factors described herein. Variations in the DNA sequences of SEQ ID NO: 1 or SEQ ID NO: 2 which are caused by point mutations or by induced modifications (including insertion, deletion, and substitution) to enhance the activity, half-life or production of the polypeptides encoded are also encompassed in the invention.

Another aspect of the present invention provides a novel method for producing chordin proteins. The method of the present invention involves culturing a suitable cell line, which has been transformed with a DNA sequence encoding a chordin protein of the invention, under the control of known regulatory sequences. The transformed host cells are cultured and the chordin proteins recovered and purified from the culture medium. The purified proteins are substantially free from other proteins with which they are co-produced as well as from other contaminants.

Suitable cells or cell lines may be mammalian cells, such as Chinese hamster ovary cells (CHO). The selection of suitable mammalian host cells and methods for transformation, culture, amplification, screening, product production and purification are known in the art. See, e.g., Gething and Sambrook, *Nature.* 293:620–625 (1981), or alternatively, Kaufman et al, *Mol. Cell. Biol.,* 5(7):1750–1759 (1985) or Howley et al, U.S. Pat. No. 4,419,446. Another suitable mammalian cell line, which is described in the accompanying examples, is the monkey COS-1 cell line. The mammalian cell CV-1 may also be suitable.

Bacterial cells may also be suitable hosts. For example, the various strains of *E. coli* (e.g., HB101, MC1061) are well-known as host cells in the field of biotechnology. Various strains of *B. subtilis,* Pseudomonas, other bacilli and the like may also be employed in this method. For expression of the protein in bacterial cells, DNA encoding the propeptide of chordin is generally not necessary.

Many strains of yeast cells known to those skilled in the art may also be available as host cells for expression of the polypeptides of the present invention. Additionally, where desired, insect cells may be utilized as host cells in the method of the present invention. See, e.g. Miller et al, *Genetic Engineering,* 8:277–298 (Plenum Press 1986) and references cited therein.

Another aspect of the present invention provides vectors for use in the method of expression of these novel chordin polypeptides. Preferably the vectors contain the full novel DNA sequences described above which encode the novel factors of the invention. Additionally, the vectors contain appropriate expression control sequences permitting expression of the chordin protein sequences. Alternatively, vectors incorporating modified sequences as described above are also embodiments of the present invention. Additionally, the sequence of SEQ ID NO: 1, SEQ ID NO: 2 or other sequences encoding chordin proteins could be manipulated to express a mature chordin protein by deleting chordin propeptide sequences and replacing them with sequences encoding the complete propeptides of other proteins, such as BMP proteins or members of the TGF-β superfamily. Thus, the present invention includes chimeric DNA molecules encoding a propeptide from a protein other than chordin, such as a member of the TGF-β superfamily linked in correct reading frame to a DNA sequence encoding a chordin polypeptide.

The vectors may be employed in the method of transforming cell lines and contain selected regulatory sequences in operative association with the DNA coding sequences of the invention which are capable of directing the replication and expression thereof in selected host cells. Regulatory sequences for such vectors are known to those skilled in the art and may be selected depending upon the host cells. Such selection is routine and does not form part of the present invention.

A protein of the present invention, which induces or influences cartilage and/or bone and/or other connective tissue formation, may have application in the healing of bone fractures and cartilage or other connective tissue defects in humans and other animals. Such a preparation employing a chordin protein may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery. A chordin-related protein may be used in the treatment of periodontal disease, and in other tooth repair processes. Such agents may provide an environment to attract bone-forming cells, affect or stimulate growth or differentiation of bone-forming cells and their progenitor cells or induce differentiation of progenitors of bone-forming cells, and may also support the regeneration of the periodontal ligament and attachment apparatus, which connects bone and teeth. Chordin polypeptides of the invention may also be useful in the treatment of systemic conditions such as osteoporosis, and under certain circumstances, to augment or inhibit the effects of osteogenic, cartilage-inducing and bone inducing factors. In addition to the TGF-β superfamily of proteins, a variety of osteogenic, cartilage-inducing and bone inducing factors have been described. See, e.g., European patent applications 148,155 and 169,016 for discussions thereof.

The proteins of the invention may also be used in wound healing and related tissue repair. The types of wounds include, but are not limited to burns, incisions and ulcers. (See, e.g. PCT Publication WO84/01106 for discussion of wound healing and related tissue repair). It is further contemplated that proteins of the invention may affect neuronal, astrocytic and glial cell survival and therefore be useful in transplantation and treatment of conditions exhibiting a decrease in neuronal survival and repair. The proteins of the invention may further be useful for the treatment of conditions related to other types of tissue, such as nerve, epidermis, muscle, and other organs such as liver, brain, lung, cardiac, pancreas and kidney tissue. The proteins of the present invention may further be useful for the treatment of relatively undifferentiated cell populations, such as embryonic cells, or stem cells, to enhance growth and/or differentiation of the cells. The proteins of the present invention may also have value as a dietary supplement, or as a component of cell culture media. For this use, the proteins may be used in intact form, or may be predigested to provide a more readily absorbed supplement.

The proteins of the invention may also have other useful properties characteristic of the TGF-β superfamily of proteins. Such properties include angiogenic, chemotactic and/or chemoattractant properties, and effects on cells including induction or inhibition of collagen synthesis, fibrosis, differentiation responses, cell proliferative responses and responses involving cell adhesion, migration and extracellular matrices. These properties make the proteins of the invention potential agents for wound healing, reduction of fibrosis and reduction of scar tissue formation.

Chordin, alone or complexed with monomrs, homodimers or heterodimers of BMPs, with members of the TGF-β superfamily of proteins, or with inhibin-α proteins or inhibin-β proteins, the chordin heterodimer is expected to demonstrate effects on the production of follicle stimulating hormone (FSH), as described further herein. It is recognized that FSH stimulates the development of ova in mammalian ovaries (Ross et al., in Textbook of Endocrinology, ed. Williams, p. 355 (1981) and that excessive stimulation of the ovaries with FSH will lead to multiple ovulations. FSH is also important in testicular function. Thus, chordin may be useful as a contraceptive based on the ability of inhibins to decrease fertility in female mammals and decrease spermatogenesis in male mammals. Administration of sufficient amounts of other inhibins can induce infertility in mammals. Chordin may also be useful as a fertility inducing therapeutic., based upon the ability of activin molecules in stimulating FSH release from cells of the anterior pituitary. See, for example, U.S. Pat. No. 4,798,885. Chordin may also be useful for advancement of the onset of fertility in sexually immature mammals, so as to increase the lifetime reproductive performance of domestic animals such as cows, sheep and pigs. It is further contemplated that chordin may be useful in modulating hematopoiesis by inducing the differentiation of erythroid cells [see, e.g., Broxmeyer et al, *Proc. Natl. Acad. Sci. USA,* 85:9052–9056 (1988) or Eto et al, *Biochem. Biophys. Res. Comm.,* 142:1095–1103 (1987)], for suppressing the development of gonadal tumors [see, e.g., Matzuk et al., *Nature,* 360:313–319 (1992)] or for augmenting the activity of bone morphogenetic proteins [see, e.g., Ogawa et al., *J. Biol. Chem.,* 267:14233–14237 (1992)].

Chordin proteins may be further characterized by their ability to modulate the release of follicle stimulating hormone (FSH) in established in vitro bioassays using rat anterior pituitary cells as described [see, e.g., Vale et al, *Endocrinology,* 91:562–572 (1972); Ling et al., *Nature,* 321:779–782 (1986) or Vale et al., *Nature,* 321:776–779 (1986)]. It is contemplated that the chordin protein of the invention may bind to TGF-β proteins, which will have different effects depending upon whether they are in homodimeric or heterodimeric form. TGF-β proteins when found as a heterodimer with inhibin α or inhibin β chains, will exhibit regulatory effects, either stimulatory or inhibitory, on the release of follicle stimulating hormone (FSH), from anterior pituitary cells as described [Ling et al., *Nature,* 321:779–782 (1986) or Vale et al., *Nature.* 321:776–779 (1986); Vale et al, *Endocrinology,* 91:562–572 (1972). Therefore, depending on the particular composition, it is expected that the chordin protein of the invention may have contrasting and opposite effects on the release of follicle stimulating hormone (FSH) from the anterior pituitary.

Activin A (the homodimeric composition of inhibin β$_A$) has been shown to have erythropoietic-stimulating activity [see e.g. Eto et al., *Biochem. Biophys. Res. Commun.,* 142:1095–1103 (1987) and Murata et al., *Proc. Natl. Acad. Sci. U.S.A.,* 85:2434–2438 (1988) and Yu et al., *Nature,* 330:765–767 (1987)]. It is contemplated that the chordin protein of the invention may have a similar erythropoietic-stimulating activity. This activity of the chordin protein may be further characterized by the ability of the chordin protein to demonstrate erythropoietin activity in the biological assay performed using the human K-562 cell line as described by [Lozzio et al., *Blood,* 45:321–334 (1975) and U.S. Pat. No. 5,071,834].

A further aspect of the invention is a therapeutic method and composition for repairing fractures and other conditions related to cartilage and/or bone and/or other connective tissue defects or periodontal diseases. The invention further comprises therapeutic methods and compositions for wound healing and tissue repair. Such compositions comprise a therapeutically effective amount of at least one of the chordin-related proteins of the invention in a mixture with a pharmaceutically acceptable vehicle, carrier or matrix. It is further contemplated that compositions of the invention may increase neuronal survival and therefore be useful in transplantation and treatment of conditions exhibiting a decrease in neuronal survival. Compositions of the invention may further include at least one other therapeutically useful agent, such as members of the TGF-β superfamily of proteins, which includes the BMP proteins BMP-1, BMP-2, BMP-3, BMP-4, BMP-5, BMP-6 and BMP-7, disclosed for instance in U.S. Pat. Nos. 5,108,922; 5,013,649; 5,116,738; 5,106,748; 5,187,076; and 5,141,905; BMP-8, disclosed in PCT publication WO91/18098; BMP-9, disclosed in PCT publication WO93/00432; BMP-10, disclosed in PCT application WO94/26893; BMP-11, disclosed in PCT application WO94/26892, BMP-12 or BMP-13, disclosed in PCT application WO95/16035, or BMP-15, disclosed in co-pending patent application, Ser. No. 08/446,924, U.S. Pat. No. 5,635,372 filed on May 18, 1995; or BMP-16, disclosed in co-pending patent application, Ser. No. 08/715,202, filed on Sep. 18, 1996. Other compositions which may also be useful include Vgr-2, and any of the growth and differentiation factors [GDFs], including those described in PCT applications WO94/15965; WO94/15949; WO95/01801; WO95/01802; WO94/21681; WO94/15966; WO95/10539; WO96/01845; WO96/02559 and others. Also useful in the present invention may be BIP, disclosed in WO94/01557; HP00269, disclosed in JP Publication number: 7-250688; and MP52, disclosed in PCT application WO93/16099. The disclosures of the above applications are hereby incorporated by reference herein.

It is expected that human chordin protein may exist in nature as homodimers or heterodimers. To promote the formation of dimers of chordin and useful proteins with increased stability, one can genetically engineer the DNA sequence of SEQUENCE ID NO: 1 to provide one or more additional cysteine residues to increase potential dimer formation. The resulting DNA sequence would be capable of producing a "cysteine added variant" of chordin. In a preferred embodiment, one would engineer the DNA sequence of SEQUENCE ID NO. 1 or SEQ ID NO: 2 so that one or more codons may be altered to a nucleotide triplet encoding a cysteine residue, such as TGT or TGC. Alternatively, one can produce "cysteine added variants" of chordin protein by altering the sequence of the protein at the amino acid level by altering one or more amino acid residues of SEQUENCE ID NO: 3 to Cys. Production of "cysteine added variants" of proteins is described in U.S. Pat. No. 5,166,322, the disclosure of which is hereby incorporated by reference.

It is expected that the proteins of the invention may act in concert with or perhaps synergistically with other related proteins and growth factors. Further therapeutic methods and compositions of the invention therefore comprises therapeutic amount of at least one chordin protein of the invention with a therapeutic amount of at least one protein growth and/or differentiation factor, such as a member of the TGF-β superfamily of proteins, such as the BMP proteins disclosed in the applications described above. Such combinations may comprise chordin with separate molecules of the BMP proteins or heteromolecules comprised of different BMP moieties. For example, a method and composition of the invention may comprise a disulfide linked dimer comprising a chordin protein subunit and a subunit from one of the "BMP" proteins described above. Thus, the present invention includes a purified chordin-related polypeptide which is a heterodimer wherein one subunit comprises the amino acid sequence from amino acid #1 to amino acid #954 of SEQ ID NO: 3, and one subunit comprises an amino acid sequence for a bone morphogenetic protein selected from the group consisting of BMP-1, BMP-2, BMP-3, BMP4, BMP-5, BMP-6, BMP-7, BMP-8, BMP-9, BMP-10, BMP-11, BMP-12 or BMP-13, disclosed in PCT application WO95/16035. VGR-2, MP-52, BIP, the GDFs, HP-269, or BMP-15, disclosed in co-pending patent application, Ser. No. 08/446,924, U.S. Pat. No. 5,635,372 filed on May 18, 1995; or BMP-16, disclosed in co-pending patent application, Ser. No. 08/715,202, filed on Sep. 18, 1996. A further embodiment may comprise a heterodimer of chordin-related moieties, for example of human chordin described herein and the *xenopus chordin* protein, which is the homologue of human chordin. Further, chordin protein may be combined with other agents beneficial to the treatment of the bone and/or cartilage and/or other connective tissue defect, wound, or tissue in question. These agents include various growth factors such as epidermal growth factor (EGF), fibroblast growth factor (FGF), platelet derived growth factor (PDGF), transforming growth factors (TGF-α and TGF-β), activins, inhibins, and k-fibroblast growth factor (kFGF), parathyroid hormone (PTH), parathyroid hormone related peptide (PTHrP). leukemia inhibitory factor (LIB/HILA/DA), insulin-like growth factors (IGF-I and IGF-II). Portions of these agents may also be used in compositions of the present invention. The preparation and formulation of such physiologically acceptable protein compositions, having due regard to pH, isotonicity, stability and the like, is within the skill of the art. The therapeutic compositions are also presently valuable for veterinary applications due to the lack of species specificity in growth and differentiation factors such as chordin. Particularly domestic animals and thoroughbred horses in addition to humans are desired patients for such treatment with the chordin proteins of the present invention.

The therapeutic method includes administering the composition topically, systemically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or other connective tissue or other tissue damage. Topical administration may be suitable for wound healing and tissue repair. Therapeutically useful agents other than the chordin proteins which may also optionally be included in the composition as described above, may alternatively or additionally, be administered simultaneously or sequentially with a BMP composition in the methods of the invention.

Preferably for bone and/or cartilage and/or other connective tissue formation, the composition includes a matrix capable of delivering chordin-related or other BMP proteins to the site of bone and/or cartilage and/or other connective tissue damage, providing a structure for the developing bone and cartilage and other connective tissue and optimally capable of being resorbed into the body. The matrix may provide slow release of chordin protein and/or other bone inductive protein, as well as proper presentation and appropriate environment for cellular infiltration. Such matrices may be formed of materials presently in use for other implanted medical applications.

The choice of matrix material is based on biocompatibility, biodegradability, mechanical properties, cosmetic appearance and interface properties. The particular application of the chordin compositions will define the appropriate formulation. Potential matrices for the compositions may be biodegradable and chemically defined calcium sulfate, tricalcium phosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalcium phosphate. The bioceramics may be altered in composition, such as in calcium-aluminate-phosphate and processing to alter pore size, particle size, particle shape, and biodegradability.

The dosage regimen will be determined by the attending physician considering various factors which modify the action of the chordin protein, e.g. amount of bone or other tissue weight desired to be formed, the site of bone or tissue damage, the condition of the damaged bone tissue, the size of a wound, type of damaged tissue, the patient's age, sex, and diet, the severity of any infection, time of administration and other clinical factors. The dosage may vary with the type of matrix used in the reconstitution and the types of BMP proteins in the composition. Generally, systemic or injectable administration will be initiated at a dose which is minimally effective, and the dose will be increased over a preselected time course until a positive effect is observed. Subsequently, incremental increases in dosage will be made limiting such incremental increases to such levels that produce a corresponding increase in effect, while taking into account any adverse affects that may appear. The addition of other known growth factors, such as IGF I (insulin like growth factor I), to the final composition, may also effect the dosage.

Progress can be monitored by periodic assessment of bone or tissue growth and/or repair. The progress can be monitored, for example, x-rays, histomorphometric determinations and tetracycline labeling.

The following examples illustrate practice of the present invention in recovering and characterizing human chordin and other chordin-related proteins, obtaining the human proteins and expressing the proteins via recombinant techniques.

EXAMPLES

Example 1 Description of the isolation of the human chordin cDNA by hybridization:

The human chordin full-length cDNA was isolated from a dT-primed cDNA library constructed in the plasmid vector pED6-dpc2. pED6-dpc2 is a derivative of the pED vector which is described in Kaufman et al., *Nucleic Acids Research*, 19:4485–4490 (1991). cDNA was made from human liver RNA purchased from Clonetech. The probe sequences used to isolate chordin were derived from genomic fragments isolated by the inventors. The sequence of the two probes were as follows: 5'-CCACGTCTCGTCCAAGGCATAGACCTT-3' (SEQ ID NO: 4) which is antisense sequence to the CR1 repeat of human chordin and 5'-CCAGCTCCGGTCACCATCAAAATAGCA-3' (SEQ ID NO: 4) which is antisense sequence to the CR3 domain of human chordin. The DNA probes were radioactively labelled with $^{32}p$ and used to screen the human liver dT-primed cDNA library, under high stringency hybridization/washing conditions, to identify clones containing sequences of the human chordin gene.

Sixty thousand library transformants were plated at a density of approximately 3000 transformants per plate on 20 plates. Nitrocellulose replicas of the transformed colonies were hybridized to the $^3P$ labelled DNA probes in standard hybridization buffer (6× SSC, 0.5% SDS, 5× Denhardt's, 10 mM EDTA pH8, 100 mg/ml Bakers Yeast ribonucleic acid) under high stringency conditions (65° C. for 2 hours). After 2 hours hybridization, the radioactively labelled DNA probe containing hybridization solution was removed and the filters were washed under high stringency conditions (2× SSC, 0.5% SDS 21° C. for 5 minutes; followed by 2× SSC, 0.1% SDS 21° C. for 15 minutes; followed by a 2nd 2× SSC, 0.1% SDS 21° C. for 15 minutes; followed by 2× SSC, 0.1% SDS 65° C. for 10 minutes). The filters were wrapped in Saran wrap and exposed to X-ray film for overnight to 3 days at −80° C., with the aid of an intensifying screen. The autoradiographs were developed and positively hybridizing transformants of various signal intensities were identified. These positive clones were picked; grown for 5 hours in selective medium and plated at low density (approximately 100 colonies per plate). Nitrocellulose replicas of the colonies were hybridized to the $^{32}P$ labelled probes in standard hybridization buffer (6× SSC, 0.5% SDS, 5× Denhardt's, 10 mM EDTA pH8, 100 mg/ml Bakers Yeast ribonucleic acid) under high stringency conditions (65° C. for 2 hours). After 2 hours hybridization, the radioactively labelled DNA probe containing hybridization solution was removed and the filters were washed under high stringency conditions (2× SSC, 0.5% SDS 21° C. for 5 minutes; followed by 2× SSC, 0.1% SDS 21° C. for 15 minutes; followed by a 2nd 2× SSC, 0.1% SDS 21° C. for 15 minutes; followed by 2× SSC, 0.1% SDS 65° C. for 10 minutes). The filters were wrapped in Saran wrap and exposed to X-ray film for overnight to 3 days at −80° C., with the aid of an intensifying screen. The autoradiographs were developed and positively hybridizing transformants were identified. Bacterial stocks of purified hybridization positive clones were made and plasmid DNA was isolated. The sequence of the cDNA insert was determined. The cDNA insert contained the sequences of both DNA probes used in the hybridization and contained the sequences for all 4 genomic fragments isolated by the inventors lab was pertained the 4 CRR domains of human chordin.

The chordin cDNA clone of SEQ ID NO: 1 was found to contain an incorrectly spliced intron that includes nucleotides #426 through #480 of the deposited cDNA clone; and contains a piece of the H. sapiens mitochondrial genome (Accession #V00662) from nucleotide #3517 through #4406 of the deposited cDNA clone. In order to overcome these problems, the inventors designed a synthetic sequence, shown in SEQ ID NO: 2, which can be used to express human chodin protein for use in the present invention.

Example 2

W-20 BIOASSAYS

A. Description of W-20 cells

Use of the W-20 bone marrow stromal cells as an indicator cell line is based upon the conversion of these cells to osteoblast-like cells after treatment with a BMP protein [Thies et al, *Journal of Bone and Mineral Research*, 5:305 (1990); and Thies et al, *Endocrinology*, 130:1318 (1992)]. Specifically, W-20 cells are a clonal bone marrow stromal cell line derived from adult mice by researchers in the laboratory of Dr. D. Nathan, Children's Hospital, Boston, Mass. Treatment of W-20 cells with certain BMP proteins results in (1) increased alkaline phosphatase production, (2) induction of PTH stimulated cAMP, and (3) induction of osteocalcin synthesis by the cells. While (1) and (2) represent characteristics associated with the osteoblast phenotype, the ability to synthesize osteocalcin is a phenotypic property only displayed by mature osteoblasts. Furthermore, to date we have observed conversion of W-20 stromal cells to osteoblast-like cells only upon treatment with BMPs. In this manner, the in vitro activities displayed by BMP treated W-20 cells correlate with the in vivo bone forming activity known for BMPs.

Below two in vitro assays useful in comparison of BMP activities of novel osteoinductive molecules are described.

B. W-20 Alkaline Phosphatase Assay Protocol

W-20 cells are plated into 96 well tissue culture plates at a density of 10,000 cells per well in 200 μl of media (DME with 10% heat inactivated fetal calf serum, 2 mM glutamine and 100 Units/ml penicillin+100 μg/ml streptomycin. The cells are allowed to attach overnight in a 95% air, 5% $CO_2$ incubator at 37° C. The 200 μl of media is removed from each well with a multichannel pipettor and replaced with an equal volume of test sample delivered in DME with 10% heat inactivated fetal calf serum, 2 mM glutamine and 1% penicillin-streptomycin. Test substances are assayed in triplicate. The test samples and standards are allowed a 24 hour incubation period with the W-20 indicator cells. After the 24 hours, plates are removed from the 37° C. incubator and the test media are removed from the cells. The W-20 cell layers are washed 3 times with 200 μl per well of calcium/magnesium free phosphate buffered saline and these washes are discarded. 50 μl of glass distilled water is added to each well and the assay plates are then placed on a dry ice/ethanol bath for quick freezing. Once frozen, the assay plates are removed from the dry ice/ethanol bath and thawed at 37° C. This step is repeated 2 more times for a total of 3 freeze-thaw procedures. Once complete, the membrane bound alkaline phosphatase is available for measurement. 50 μl of assay mix (50 mM glycine. 0.05 % Triton X-100, 4 mM $MgCl_2$, 5 mM p-nitrophenol phosphate, pH=10.3) is added to each assay well and the assay plates are then incubated for 30 minutes at 37° C. in a shaking waterbath at 60 oscillations per minute. At the end of the 30 minute incubation, the reaction is stopped by adding 100 μl of 0.2N NaOH to each well and placing the assay plates on ice. The spectrophotometric absorbance for each well is read at a wavelength of 405 nanometers. These values are then compared to known standards to give an estimate of the alkaline phosphatase activity in each sample. For example, using known amounts of p-nitrophenol phosphate, absorbance values are generated. This is shown in Table I.

TABLE I

Absorbance Values for Known Standards of P-Nitrophenol Phosphate

| P-nitrophenol phosphate umoles | Mean absorbance (405 nm) |
|---|---|
| 0.000 | 0 |
| 0.006 | 0.261 +/− .024 |
| 0.012 | 0.521 +/− .031 |
| 0.018 | 0.797 +/− .063 |
| 0.024 | 1.074 +/− .061 |
| 0.030 | 1.305 +/− .083 |

Absorbance values for known amounts of BMPs can be determined and converted to μmoles of p-nitrophenol phosphate cleaved per unit time as shown in Table II.

TABLE II

Alkaline Phosphatase Values for W-20 Cells Treating with BMP-2

| BMP-2 concentration ng/ml | Absorbance Reading 405 nmeters | umoles substrate per hour |
|---|---|---|
| 0 | 0.645 | 0.024 |
| 1.56 | 0.696 | 0.026 |
| 3.12 | 0.765 | 0.029 |
| 6.25 | 0.923 | 0.036 |
| 12.50 | 1.121 | 0.044 |
| 25.0 | 1.457 | 0.058 |
| 50.0 | 1.662 | 0.067 |
| 100.0 | 1.977 | 0.080 |

These values are then used to compare the activities of known amounts of BMP-16 to BMP-2.

C. Osteocalcin RIA Protocol

W-20 cells are plated at $10^6$ cells per well in 24 well multiwell tissue culture dishes in 2 mls of DME containing 10% heat inactivated fetal calf serum, 2 mM glutamine. The cells are allowed to attach overnight in an atmosphere of 95% air 5% $CO_2$ at 37° C. The next day the medium is changed to DME containing 10% fetal calf serum, 2 mM glutamine and the test substance in a total volume of 2 ml. Each test substance is administered to triplicate wells. The test substances are incubated with the W-20 cells for a total of 96 hours with replacement at 48 hours by the same test medias. At the end of 96 hours, 50 μl of the test media is removed from each well and assayed for osteocalcin production using a radioimmunoassay for mouse osteocalcin. The details of the assay are described in the kit manufactured by Biomedical Technologies Inc., 378 Page Street, Stoughton, Mass. 02072. Reagents for the assay are found as product numbers BT-431 (mouse osteocalcin standard), BT-432 (Goat anti-mouse Osteocalcin), BT-431R (iodinated mouse osteocalcin), BT-415 (normal goat serum) and BT-414 (donkey anti goat IgG). The RIA for osteocalcin synthesized by W-20 cells in response to BMP treatment is carried out as described in the protocol provided by the manufacturer.

The values obtained for the test samples are compared to values for known standards of mouse osteocalcin and to the amount of osteocalcin produced by W-20 cells in response to challenge with known amounts of BMP-2. The values for BMP-2 induced osteocalcin synthesis by W-20 cells is shown in Table III.

TABLE III

Osteocalcin Synthesis by W-20 Cells

| BMP-2 Concentration ng/ml | Osteocalcin Synthesis ng/well |
|---|---|
| 0 | 0.8 |
| 2 | 0.9 |
| 4 | 0.8 |
| 8 | 2.2 |
| 16 | 2.7 |
| 31 | 3.2 |
| 62 | 5.1 |
| 125 | 6.5 |
| 250 | 8.2 |
| 500 | 9.4 |
| 1000 | 10.0 |

Example 3

ROSEN MODIFIED SAMPATH-REDDI ASSAY

A modified version of the rat bone formation assay described in Sampath and Reddi, *Proc. Natl. Acad. Sci. USA*, 80:6591–6595 (1983) is used to evaluate bone and/or cartilage and/or other connective tissue activity of BMP proteins. This modified assay is herein called the Rosen-modified Sampath-Reddi assay. The ethanol precipitation step of the Sampath-Reddi procedure is replaced by dialyzing (if the composition is a solution) or diafiltering (if the composition is a suspension) the fraction to be assayed against water. The solution or suspension is then equilibrated to 0.1% TFA. The resulting solution is added to 20 mg of rat matrix. A mock rat matrix sample not treated with the protein serves as a control. This material is frozen and lyophilized and the resulting powder enclosed in #5 gelatin capsules. The capsules are implanted subcutaneously in the abdominal thoracic area of 21–49 day old male Long Evans rats. The implants are removed after 7–14 days. Half of each implant is used for alkaline phosphatase analysis [see. Reddi et al. *Proc. Natl. Acad. Sci.,* 69:1601 (1972)].

The other half of each implant is fixed and processed for histological analysis. 1 μm glycolmethacrylate sections are stained with Von Kossa and acid fuschin to score the amount of induced bone and cartilage and other connective tissue formation present in each implant. The terms +1 through +5 represent the area of each histological section of an implant occupied by new bone and/or cartilage cells and matrix. A score of +5 indicates that greater than 50% of the implant is new bone and/or cartilage produced as a direct result of protein in the implant. A score of +4, +3, +2, and +1 would indicate that greater than 40%, 30%, 20% and 10% respectively of the implant contains new cartilage and/or bone.

Alternatively, the implants are inspected for the appearance of tissue resembling embryonic tendon, which is easily recognized by the presence of dense bundles of fibroblasts oriented in the same plane and packed tightly together. [Tendon/ligament-like tissue is described, for example, in Ham and Cormack, *Histology* (JB Lippincott Co. (1979), pp. 367–369, the disclosure of which is hereby incorporated by reference]. These findings may be reproduced in additional assays in which tendon/ligament-like tissues are observed in the chordin-related protein containing implants. The chordin-related proteins of this invention may be assessed for activity on this assay.

Example 4

Expression of Chordin

In order to produce murine, human or other mammalian chordin-related proteins, the DNA encoding it is transferred into an appropriate expression vector and introduced into mammalian cells or other preferred eukaryotic or prokaryotic hosts by conventional genetic engineering techniques. The preferred expression system for biologically active recombinant human chordin is contemplated to be stably transformed mammalian cells.

One skilled in the art can construct mammalian expression vectors by employing the sequence of SEQ ID NO: 1 or SEQ ID NO: 3, or other DNA sequences encoding chordin-related proteins or other modified sequences and known vectors, such as pCD [Okayama et al., *Mol. Cell Biol.*, 2:161–170 (1982)], pJL3, pJL4 [Gough et al., *EMBO J.*, 4:645–653 (1985)] and pMT2 CXM.

The mammalian expression vector pMT2 CXM is a derivative of p91023(b) (Wong et al., Science 228:810–815, 1985) differing from the latter in that it contains the ampicillin resistance gene in place of the tetracycline resistance gene and further contains a XhoI site for insertion of cDNA clones. The functional elements of pMT2 CXM have been described (Kaufman, R. J., 1985, Proc. Natl. Acad. Sci. USA 82:689–693) and include the adenovirus VA genes, the SV40 origin of replication including the 72 bp enhancer, the adenovirus major late promoter including a 5' splice site and the majority of the adenovirus tripartite leader sequence present on adenovirus late mRNAs, a 3' splice acceptor site, a DHFR insert, the SV40 early polyadenylation site (SV40), and pBR322 sequences needed for propagation in *E. coli*.

Plasmid pMT2 CXM is obtained by EcoRI digestion of pMT2-VWF, which has been deposited with the American Type Culture Collection (ATCC), Rockville, Md. (USA) under accession number ATCC 67122. EcoRI digestion excises the cDNA insert present in pMT2VWF, yielding pMT2 in linear form which can be ligated and used to transform *E. coli* HB 101 or DH-5 to ampicillin resistance. Plasmid pMT2 DNA can be prepared by conventional methods. pMT2 CXM is then constructed using loopoutlin mutagenesis [Morinaga, et al., *Biotechnology* 84: 636 (1984). This removes bases 1075 to 1145 relative to the Hind III site near the SV40 origin of replication and enhancer sequences of pMT2. In addition it inserts the following sequence:

5'PO-CATGGGCAGCTCGAG-3'(SEQ ID NO:5)

at nucleotide 1145. This sequence contains the recognition site for the restriction endonuclease Xho I. A derivative of pMT2CXM, termed pMT23, contains recognition sites for the restriction endonucleases PstI, Eco RI, SalI and XhoI. Plasmid pMT2 CXM and pMT23 DNA may be prepared by conventional methods.

pEMC2β1 derived from pMT21 may also be suitable in practice of the invention. pMT21 is derived from pMT2 which is derived from pMT2-VWF. As described above EcoRI digestion excises the cDNA insert present in pMT-VWF, yielding pMT2 in linear form which can be ligated and used to transform *E. Coli* HB 101 or DH-5 to ampicillin resistance. Plasmid pMT2 DNA can be prepared by conventional methods.

pMT21 is derived from pMT2 through the following two modifications. First, 76 bp of the 5' untranslated region of the DHFR cDNA including a stretch of 19 G residues from G/C tailing for cDNA cloning is deleted. In this process, a XhoI site is inserted to obtain the following sequence immediately upstream from DHFR: 5'-<u>CTGCAGG</u>CGAGCCT<u>GAATTCCTCGAG</u>CC<u>ATG</u>-3' (SEQ ID NO:6)
                PstI         Eco RI XhoI Second, a unique ClaI site is introduced by digestion with EcoRV and XbaI, treatment with Klenow fragment of DNA polymerase I, and ligation to a ClaI linker (CATCGATG). This deletes a 250 bp segment from the adenovirus associated RNA (VAI) region but does not interfere with VAI RNA gene expression or function. pMT21 is digested with EcoRI and XhoI, and used to derive the vector pEMC2B1.

A portion of the EMCV leader is obtained from pMT2-ECAT1 [S. K. Jung, et al. *J. Virol* 63:1651–1660 (1989)] by digestion with Eco RI and PstI, resulting in a 2752 bp fragment. This fragment is digested with TaqI yielding an Eco RI-TaqI fragment of 508 bp which is purified by electrophoresis on low melting agarose gel. A 68 bp adapter and its complementary strand are synthesized with a 5' TaqI protruding end and a 3' XhoI protruding end which has the following sequence:

5'-<u>CGA</u>GGTTAAAAAACGTCTAGGCCCCCCGAACCACGGGGACGTGGTTTTCCTTT   (SEQ ID NO: 7)
   TaqI

GAAAAACACG<u>ATT</u>GC-3'
           XhoI

This sequence matches the EMC virus leader sequence from nucleotide 763 to 827. It also changes the ATG at position 10 within the EMC virus leader to an ATT and is followed by a XhoI site. A three way ligation of the pMT21 Eco RI-16hoI fragment, the EMC virus EcoRI-TaqI fragment, and the 68 bp oligonucleotide adapter TaqI-16hoI adapter resulting in the vector pEMC2β1.

This vector contains the SV40 origin of replication and enhancer, the adenovirus major late promoter, a cDNA copy of the majority of the adenovirus tripartite leader sequence, a small hybrid intervening sequence, an SV40 polyadenylation signal and the adenovirus VA I gene, DHFR and β-lactamase markers and an EMC sequence, in appropriate relationships to direct the high level expression of the desired cDNA in mammalian cells.

The construction of vectors may involve modification of the chordin-related DNA sequences. For instance, chordin cDNA can be modified by removing the non-coding nucleotides on the 5' and 3' ends of the coding region. The deleted non-coding nucleotides may or may not be replaced by other sequences known to be beneficial for expression. These vectors are transformed into appropriate host cells for expression of chordin-related proteins. Additionally, the sequence of SEQ ID NO: 1 or SEQ ID NO: 3 or other sequences encoding chordin-related proteins can be manipulated to express a mature chordin-related protein by deleting chordin encoding propeptide sequences and replacing them with sequences encoding the complete propeptides of other BMP proteins.

One skilled in the art can manipulate the sequences of SEQ ID NO: 1 by eliminating or replacing the mammalian regulatory sequences flanking the coding sequence with bacterial sequences to create bacterial vectors for intracellular or extracellular expression by bacterial cells or other prokaryotic hosts. For example, the coding sequences could be further manipulated (e.g. ligated to other known linkers or modified by deleting non-coding sequences therefrom or altering nucleotides therein by other known techniques). The modified chordin-related coding sequence could then be inserted into a known bacterial vector using procedures such as described in T. Taniguchi et al., *Proc. Natl Acad. Sci. USA*, 77:5230–5233 (1980). This exemplary bacterial vector could then be transformed into bacterial host cells and a chordin-related protein expressed thereby. For a strategy for producing extracellular expression of chordin-related proteins in bacterial cells, see, e.g. European patent application EPA 177,343. Alternatively, high level expression of chordin-related protein in bacterial cells, particularly, *E. coli* cells, may be achieved by fusion of the chordin coding sequence to the 3' end of the gene for the native *E. coli* protein thioredoxin. LaVallie et al., *Bio/Technology*, 11: 187–192 (1993).

Similar manipulations can be performed for the construction of an insect vector [See, e.g. procedures described in published European patent application 155,476] for expression in insect cells. A yeast vector could also be constructed employing yeast regulatory sequences for intracellular or extracellular expression of the factors of the present invention by yeast cells. [See, e.g., procedures described in published PCT application WO86/00639 and European patent application EPA 123,289].

A method for producing high levels of a chordin-related protein of the invention in mammalian cells may involve the construction of cells containing multiple copies of the heterologous chordin-related gene. The heterologous gene is linked to an amplifiable marker, e.g. the dihydrofolate reductase (DHFR) gene for which cells containing increased gene copies can be selected for propagation in increasing concentrations of methotrexate (MTX) according to the procedures of Kaufman and Sharp, *J. Mol. Biol.*, 159:601–629 (1982). This approach can be employed with a number of different cell types.

For example, a plasmid containing a DNA sequence for a chordin-related protein of the invention in operative association with other plasmid sequences enabling expression thereof and the DHFR expression plasmid pAdA26SV(A)3 [Kaufman and Sharp, *Mol. Cell. Biol.*, 2:1304 (1982)] can be co-introduced into DHFR-deficient CHO cells, DUKX-BII, by various methods including calcium phosphate coprecipitation and transfection, electroporation or protoplast fusion. DHFR expressing transformants are selected for growth in alpha media with dialyzed fetal calf serum, and subsequently selected for amplification by growth in increasing concentrations of MTX (e.g. sequential steps in 0.02, 0.2. 1.0 and 5 uM MTX) as described in Kaufman et al., *Mol Cell Biol.*, 5:1750 (1983). Transformants are cloned, and biologically active chordin expression is monitored by the Rosen-modified Sampath-Reddi rat bone formation assay described above in Example 3, or by BMP binding as shown in Example 8. Chordin protein expression should increase with increasing levels of MTX resistance. Chordin polypeptides are characterized using standard techniques known in the art such as pulse labeling with [35S] methionine or cysteine and polyacrylamide gel electrophoresis. Similar procedures can be followed to produce other chordin-related proteins.

Example 5

Biological Activity of Expressed Chordin

To measure the biological activity of the expressed chordin-related proteins obtained in Example 4 above, the proteins are recovered from the cell culture and purified by isolating the chordin-related proteins from other proteinaceous materials with which they are co-produced as well as from other contaminants. The purified protein may be assayed in accordance with the rat bone formation assay described in Example 3.

Purification is carried out using standard techniques known to those skilled in the art.

Protein analysis is conducted using standard techniques such as SDS-PAGE acrylamide [Laemmli, *Nature* 227:680 (1970)] stained with silver [Oakley, et al. *Anal. Biochem.* 105:361 (1980)] and by immunoblot [Towbin, et al. *Proc. Natl. Acad. Sci. USA* 76:4350 (1979)]

Example 6 Northern Analyses

Using Northern analysis, chordin and chordin-related proteins can be tested for their effects on various cell lines. Suitable cell lines include cell lines derived from E13 mouse limb buds. After 10 days of treatment with chordin or chordin-related protein, the cell phenotype is examined histologically for indications of tissue differentiation. In addition, Northern analysis of mRNA from chordin or chordin-related protein treated cells can be performed for various markers including one or more of the following markers for bone, cartilage and/or tendon/ligament, as described in Table IV:

TABLE IV

| Marker | Bone | Cartilage | Tendon/Ligament |
|---|---|---|---|
| Osteocalcin | + | − | − |
| Alkaline Phosphatase | + | − | − |
| Proteoglycan Core Protein | +/−[1] | + | +[2] |
| Collagen Type I | + | + | + |
| Collagen Type II | +/−[1] | + | +[2] |
| Decorin | + | + | + |
| Elastin | +/−[3] | ? | + |

[1]Marker seen early, marker not seen as mature bone tissue forms
[2]Marker depends upon site of tendon; strongest at bone interface
[3]Marker seen at low levels Example 7

Embryonic Stem Cell Assay

In order to assay the effects of the chordin proteins of the present invention, it is possible to assay the growth and differentiation effects in vitro on a number of available embryonic stem cell lines. One such cell line is ES-E14TG2, which is available from the American Type Culture Collection in Rockville, Md.

In order to conduct the assay, cells may be propagated in the presence of 100 units of LIF to keep them in an undifferentiated state. Assays are setup by first removing the LIF and aggregating the cells in suspension, in what is known as embryoid bodies. After 3 days the embryoid bodies are plated on gelatin coated plates (12 well plates for PCR analysis, 24 well plates for immunocytochemistry) and treated with the proteins to be assayed. Cells are supplied with nutrients and treated with the protein factor every 2–3 days. Cells may be adapted so that assays may be conducted in media supplemented with 15% Fetal Bovine Serum (FBS) or with CDM defined media containing much lower amounts of FBS.

At the end of the treatment period (ranging from 7–21 days) RNA is harvested from the cells and analyzed by quantitative multiplex PCR for the following markers:

Brachyury, a mesodermal marker, AP-2, an ectodermal marker, and HNF-3α an endodermal marker. Through immunocytochemistry, it is also possible to detect the differentiation of neuronal cells (glia and neurons), muscle cells (cardiomyocytes, skeletal and smooth muscle), and various other phenotype markers such as proteoglycan core protein (cartilage), and cytokeratins (epidermis). Since these cells have a tendency to differentiate autonomously when LIF is removed, the results are always quantitated by comparison to an untreated control.

Example 8

BMP Binding

The chordin and chordin-related polypeptides of the present invention may be assayed for binding to BMPs, other TGF-β proteins, or other ligands in any manner known in the art, including the following methods:

Ligand Blotting: The binding protein [chordin or chordin-related polypeptide] is run on SDS-PAGE, transferred to a membrane (such as a Western blot) and probed with iodinated ligand. Fukui et al., *Developmental Biology.* 159:131–139 (1993).

Gel Filtration: The binding protein [chordin or chordin-related polypeptide] is incubated with iodinated ligand and and ligand-binding protein complex is separated from unbound species by size using gel filtration. Vaughn and Vale, *Endocrinology,* 132:2038–2050 (1993).

Cross-Linking: The binding protein [chordin or chordin-related polypeptide] is incubated with iodinated ligand and covalently coupled with chemical cross-linker. The reaction mix is run on SDS-PAGE. Autoradiography will reveal complex formation via binding of ligand to binding protein. Vaughn and Vale, *Endocrinology,* 132:2038–2050 (1993).

Immunoprecipitation: The binding protein [chordin or chordin-related polypeptide] is incubated with iodinated ligand and covalently coupled with chemical cross-linker. The reaction mix is then immunoprecipitated with ligand antibody. The immunoprecipitate is run on SDS-PAGE. Vaughn and Vale, *Endocrinology,* 132:2038–2050 (1993).

Gel Shift: The binding protein [chordin or chordin-related polypeptide] is incubated with iodinated ligand and run on non-denaturing agarose gel. The complex is identified by autoradiography. Krumment at al., *Endocrinology,* 132:431443 (1993).

Radioreceptor Binding Assay: The ligand is iodinated and specific activity is determined. The cell surface receptor binding assay described in Massague, *Methods in Enzymology,* 46:174–195 (1987) is performed using 10T1/2 cells, or other suitable cell line. The cells are allowed to reach confluency in suitable medium, rinsed, and incubated with iodinated ligand containing increasing concentrations of binding protein [chordin or chordin-related polypeptide] at room temperature for one hour. The plates are chilled and rinsed. The bound iodinated ligand is solubilized with solubilization buffer and counted with a gamma counter. Massague, Id.

The above references are hereby incorporated herein by reference for their full disclosure of the methods and materials useful in the above procedures.

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

ATCC Deposits

The following materials have been deposited with the American Type Culture Collection (ATCC), Rockville, Md. (USA) under the Budapest Treaty. pCHD__1A/DH10B, a plasmid containing the DNA sequence of human chordin [SEQ ID NO: 1] was deposited on Nov. 12, 1996. ATCC accession number ATCC 98258.

What is claimed is:

1. A purified chordin polypeptide comprising the amino acid sequence from amino acid #1 to #954 as set forth in SEQ ID NO: 3.

2. A purified chordin polypeptide produced by the steps of
(a) culturing a cell transformed with a DNA molecule encoding said polypeptide, wherein said polypeptide comprises the amino acid sequence from amino acid #1 to #954 as set forth in SEQ ID NO: 3; and
(b) recovering and purifying said polypeptide from the culture medium of said cell.

3. A polypeptide complex comprising a purified chordin polypeptide and a transforming growth factor-$\beta$ (TGF-$\beta$) superfamily member, wherein said chordin polypeptide comprises the amino acid sequence from amino acid #1 to #954 as set forth in SEQ ID NO: 3.

4. The complex of claim 3, wherein said TGF-$\beta$ superfamily member is selected from the group consisting of BMP-1, BMP-2, BMP-3, BMP-4, BMP-5, BMP-6, BMP-7, BMP-8, BMP-9, BMP-10, BMP-11, BMP-12, BMP-13, Vgr-2, HP-269, MP52, BIP, BMP-15, and BMP-16.

5. A polypeptide heterodimer comprising a purified chordin polypeptide subunit, wherein said chordin polypeptide subunit comprises the amino acid sequence from amino acid #1 to #954 as set forth in SEQ ID NO: 3, and a subunit comprising the amino acid sequence of a bone morphogenetic protein, wherein said bone morphogenetic protein is selected from the group consisting of BMP-1, BMP-2, BMP-3, BMP-4, BMP-5, BMP-6, BMP-7, BMP-8, BMP-9, BMP-10, BMP-11, BMP-12, BMP-13, Vgr-2, HP-269, MP52, BIP, BMP-15, and BMP-16.

* * * * *